United States Patent
Schulhauser et al.

(10) Patent No.: US 9,913,693 B2
(45) Date of Patent: Mar. 13, 2018

(54) ERROR CORRECTION TECHNIQUES IN SURGICAL NAVIGATION

(75) Inventors: Randal C. Schulhauser, Phoenix, AZ (US); Paul Gerrish, Phoenix, AZ (US); Michael F. Mattes, Chandler, AZ (US); Todd A. Kallmyer, Tempe, AZ (US); Patrick P. Senarith, Tustin, CA (US); Per Klype, Phoenix, AZ (US); David A. Ruben, Mesa, AZ (US)

(73) Assignee: Medtronic, Inc., Minneapolis, MN (US)

( * ) Notice: Subject to any disclaimer, the term of this patent is extended or adjusted under 35 U.S.C. 154(b) by 1313 days.

(21) Appl. No.: 12/916,232

(22) Filed: Oct. 29, 2010

(65) Prior Publication Data

US 2012/0108954 A1    May 3, 2012

(51) Int. Cl.
   *A61B 5/05*    (2006.01)
   *A61B 34/20*    (2016.01)
   *A61B 17/00*    (2006.01)
   *A61B 90/00*    (2016.01)

(52) U.S. Cl.
   CPC .... *A61B 34/20* (2016.02); *A61B 2017/00703* (2013.01); *A61B 2034/2048* (2016.02); *A61B 2034/2051* (2016.02); *A61B 2034/2055* (2016.02); *A61B 2034/2072* (2016.02); *A61B 2090/0818* (2016.02); *A61B 2090/376* (2016.02)

(58) Field of Classification Search
   None
   See application file for complete search history.

(56) References Cited

U.S. PATENT DOCUMENTS

| | | | |
|---|---|---|---|
| 6,122,538 A * | 9/2000 | Sliwa, Jr. | A61B 8/00 324/207.14 |
| 6,332,089 B1 * | 12/2001 | Acker | A61B 5/0422 128/899 |
| 6,484,118 B1 | 11/2002 | Govari | |
| 2003/0100925 A1 * | 5/2003 | Pape | A61N 1/36514 607/17 |
| 2005/0085720 A1 | 4/2005 | Jascob et al. | |
| 2006/0058604 A1 | 3/2006 | Avinash et al. | |
| 2006/0066295 A1 * | 3/2006 | Tamura et al. | 324/202 |
| 2006/0213267 A1 * | 9/2006 | Tronconi et al. | 73/510 |
| 2007/0259690 A1 * | 11/2007 | Julian et al. | 455/557 |

(Continued)

FOREIGN PATENT DOCUMENTS

| CN | 101410724 A | 4/2009 |
|---|---|---|
| DE | 102005037426 A1 | 2/2007 |

(Continued)

OTHER PUBLICATIONS

International Search Report and Written Opinion of PCT/US2011/034547, dated Oct. 19, 2011, 13 pp.

(Continued)

*Primary Examiner* — James Kish

(57) ABSTRACT

A medical system includes a sensor location module, a first module, and a second module. The sensor location module determines a location of a magnetic field sensor within a magnetic field. The first module determines an acceleration of the magnetic field sensor. The second module indicates a modified location of the magnetic field sensor in an image of a medical patient based on the acceleration and one or more previously determined locations.

24 Claims, 16 Drawing Sheets

(56) References Cited

U.S. PATENT DOCUMENTS

| | | | |
|---|---|---|---|
| 2007/0270686 A1* | 11/2007 | Ritter | A61B 5/06 600/424 |
| 2008/0146941 A1 | 6/2008 | Dala-Krishna | |
| 2008/0161681 A1* | 7/2008 | Hauck | A61B 5/06 600/424 |
| 2009/0149740 A1* | 6/2009 | Hoheisel | A61B 19/5244 600/424 |
| 2009/0303204 A1* | 12/2009 | Nasiri et al. | 345/184 |
| 2010/0125194 A1* | 5/2010 | Bonner et al. | 600/424 |
| 2010/0137705 A1 | 6/2010 | Jensen et al. | |
| 2010/0160772 A1 | 6/2010 | Gardeski et al. | |
| 2010/0168556 A1 | 7/2010 | Shen et al. | |
| 2010/0168559 A1 | 7/2010 | Tegg et al. | |

FOREIGN PATENT DOCUMENTS

| | | |
|---|---|---|
| WO | 0039576 A1 | 7/2000 |
| WO | 2007103362 A2 | 9/2007 |

OTHER PUBLICATIONS

International Preliminary Report on Patentability from International Application No. PCT/US2011/034547, dated Apr. 30, 2013, 7 pp.

Response to Communication under Rule 161(1) EPC from counterpart European Application No. 11738849.6, filed on Jan. 10, 2017, 5 pp.

Preliminary Amendments from counterpart European Application No. 11738849.6, filed on May 27, 2013, 9 pp.

Communication pursuant to Article 94(3) EPC from counterpart European Application No. 11738849.6, dated Jun. 17, 2015, 5 pp.

Response to Communication dated Jun. 17, 2015, from counterpart European Application No. 11738849.6, filed on Sep. 17, 2015, 6 pp.

Intent to Grant from counterpart European Application No. 11738849.6, dated Feb. 8, 2016, 68 pp.

* cited by examiner

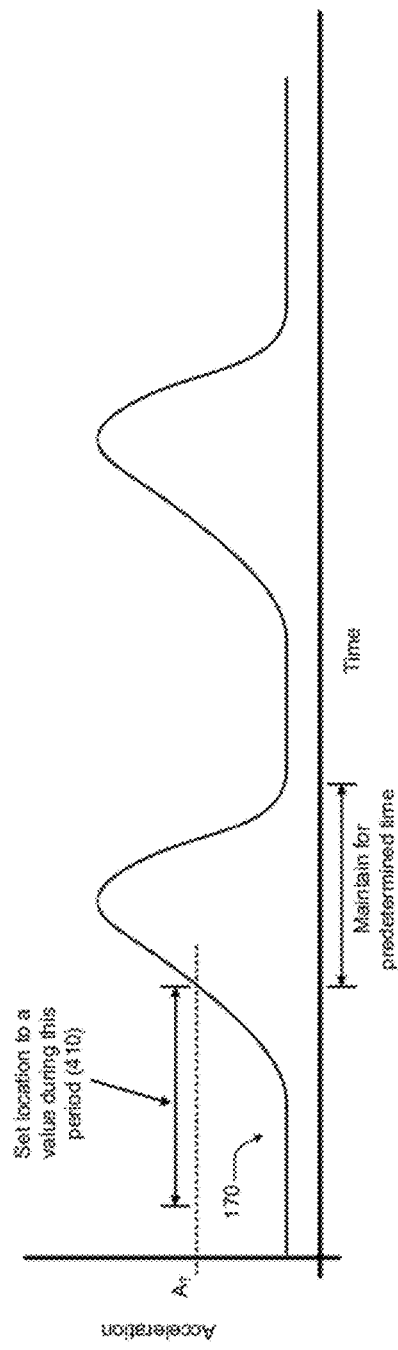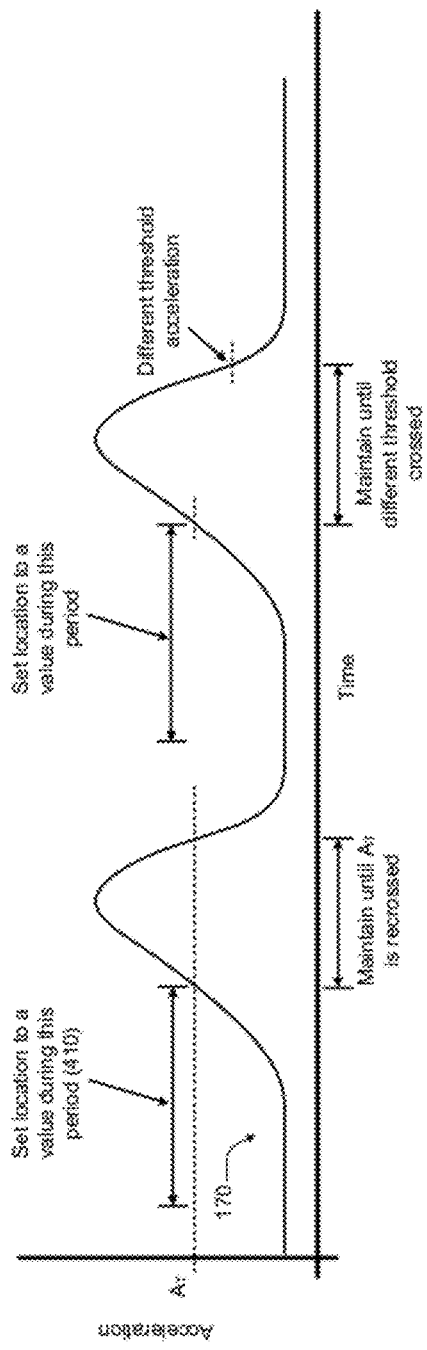

ERROR CORRECTION TECHNIQUES IN SURGICAL NAVIGATION

TECHNICAL FIELD

The disclosure relates to surgical navigation, and, more particularly, to positional accuracy in surgical navigation systems.

BACKGROUND

Surgical navigation systems track the location of a medical instrument used during a medical procedure and display the location of the instrument on a display for clinician review. Surgical navigation systems may include an imaging device that acquires images of a patient undergoing the procedure, a tracking system that tracks the location of the medical instrument, and a computing device that provides the computational resources used to track the instrument and display the location of the instrument in relation to the acquired patient images. Images displayed by the surgical navigation system may include an instrument icon that is superimposed over the acquired patient images to indicate a location of the instrument relative to the patient's anatomy.

Surgical navigation systems may include a variety of tracking systems. In some examples, optical tracking systems may include an infrared emitter that emits an infrared signal, tracking spheres that reflect the signals, and cameras that pick up the reflected signals. An instrument may be equipped with the tracking spheres that reflect the infrared signals. The cameras in the optical tracking system may pick up the reflected signals and a computing device may triangulate the position of the instrument based on the reflected signals, allowing the optical tracking system to triangulate the position of the instrument. In other examples, electromagnetic tracking systems may include an electromagnetic field emitter that generates an electromagnetic field and a magnetic field sensor that generates signals in response to the field. An instrument may be equipped with the magnetic field sensor and a computing device may analyze signals received from the magnetic field sensor to determine the location of the magnetic field sensor in the magnetic field.

SUMMARY

The accuracy of a surgical navigation systems may vary when mapping an instrument icon onto an acquired patient image in some circumstances. For example, surgical navigation systems may map the instrument icon onto a patient image in an incorrect location under conditions when the tracked instrument (i.e., sensor) experiences an amount of motion that is not accurately represented in the patient image. This incorrect image mapping of the instrument icon onto the patient image may negate some of the benefits provided to a clinician using the surgical navigation system.

A surgical navigation system according to an example of the present disclosure includes a motion sensor (e.g., an inertial sensor), such as an accelerometer and/or gyroscopic sensor, that may be used to compensate for errors arising from motion of the instrument that may cause an incorrect mapping. For example, the system of the present disclosure may measure motion of the tracked instrument based on signals received from the motion sensor, and then, based on the detected motion, the system may account for motion of the tracked instrument when mapping the location of the instrument onto the patient image. In this manner, the system may compensate for errors that may arise due to motion of the instrument.

In one example according to the present disclosure, a medical system comprises a sensor location module, a first module, and a second module. The sensor location module determines a location of a magnetic field sensor within a magnetic field. The first module determines an acceleration of the magnetic field sensor. The second module indicates a modified location of the magnetic field sensor in an image of a medical patient based on the acceleration and one or more previously determined locations.

In another example according to the present disclosure, a method comprises determining a location of a magnetic field sensor within a magnetic field, determining an acceleration of the magnetic field sensor, and indicating a modified location of the magnetic field sensor in an image of a medical patient based on the acceleration and one or more previously determined locations.

In another example according to the present disclosure, a medical system comprises a magnetic field sensor, a motion sensor, an instrument including the magnetic field sensor and the motion sensor, and a module. The module determines a location of the magnetic field sensor within a magnetic field based on signals received from the magnetic field sensor and determines an amount of motion of the magnetic field sensor based on signals received from the motion sensor. Additionally, the module indicates a modified location of the magnetic field sensor in an image of a medical patient based on the amount of motion and one or more previously determined locations.

The details of one or more examples are set forth in the accompanying drawings and the description below. Other features, objects, and advantages will be apparent from the description and drawings, and from the claims.

BRIEF DESCRIPTION OF THE DRAWINGS

FIGS. 11A-11B illustrate another set of example acceleration curve traces versus time as received by the threshold detection module of FIG. 8.

DETAILED DESCRIPTION

Figure 1:
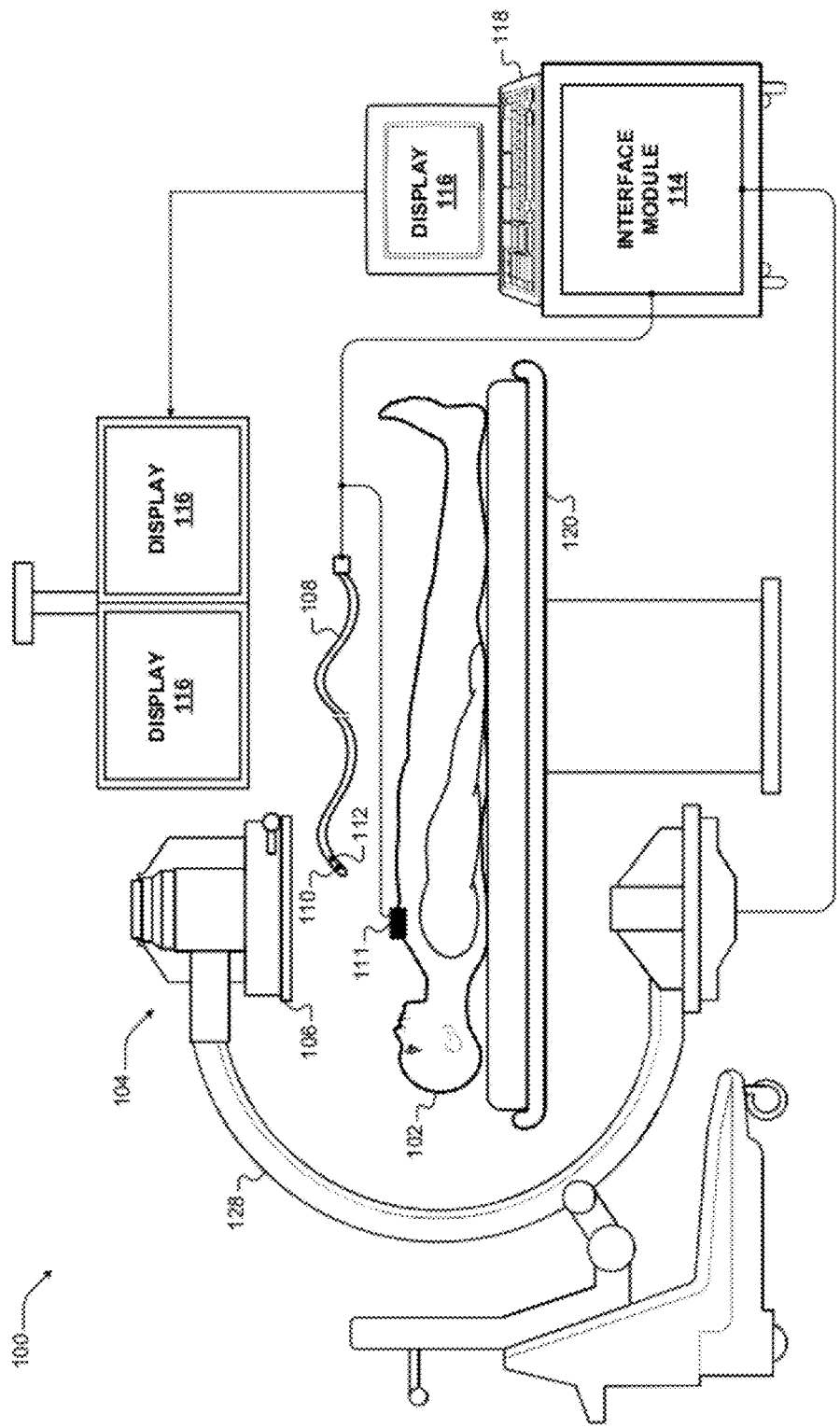
FIG. 1 shows an example surgical navigation system.

FIG. 1 illustrates an example surgical navigation system 100. One or more clinicians (not shown) may use surgical navigation system 100 to perform various surgical navigation procedures on patient 102. For example, surgical navigation procedures may include, but are not limited to, cardiac catheterization procedures, cranial neurosurgery, spine surgery, orthopedics, or implantation of electrical leads, fluid catheters, or other implantable medical devices. In some examples, the surgical navigation procedures most applicable to error correction may be procedures that include the most tortuous paths or shifts in patient anatomy due to movement or a beating heart (e.g., cardiac procedures). Additionally, the surgical navigation procedures may be applicable to precision procedures such as neurosurgery. As used herein, a procedure may generally refer to the use of surgical navigation system 100 by a clinician to provide therapy to patient 102.

Surgical navigation system 100 may include an imaging device 104, an electromagnetic (EM) field emitter 106, a surgical instrument 108 (e.g., a catheter) that includes an instrument sensor 110 and an accelerometer 112, a reference sensor 111, an interface module 114, and a display 116. Imaging device 104 acquires images of patient 102 which are subsequently processed by interface module 114 and displayed on display 116. Images acquired by imaging device 104 may include, for example, images of the patients body, or parts thereof, that may be used during the surgical navigation procedure to provide therapy or to reveal or diagnose disease. Surgical navigation system 100 may also include a user interface 118 that the clinician may use to interface with the surgical navigation system. User interface 118 may include, for example, a keyboard, a pointing device such as a mouse, or other controller.

Interface module 114, interface module 130, and modules included within interface modules 114, 130 may represent any computing device capable of performing the functions attributed to interface modules 114, 130 in the present disclosure. In some examples, interface modules 114, 130 may include dedicated hardware with dedicated software for implementing the functionality of interface modules 114, 130. In other examples, interface modules 114, 130 may represent off-the-shelf computing devices, such as a desktop or laptop computer, running an application that enables interface modules 114, 130 to provide the functionality attributed to interface modules 114, 130.

In still other examples, the modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Furthermore, the modules may comprise memory that may include computer-readable instructions that, when executed by one or more processors, cause the modules to perform various functions attributed to the modules herein. Memory may include any volatile, non-volatile, magnetic, or electrical media, such as a random access memory (RAM), read-only memory (ROM), non-volatile RAM (NVRAM), electrically-erasable programmable ROM (EEPROM), flash memory, or any other digital media.

The modules of the present disclosure may also comprise any one or more of an application specific integrated circuit (ASIC), a microprocessor, a microcontroller, a digital signal processor (DSP), a field-programmable gate array (FPGA), or equivalent discrete or integrated logic circuitry. In some examples, modules may include multiple components, such as any combination of one or more microprocessors, one or more microcontrollers, one or more DSPs, one or more ASICs, or one or more FPGAs.

The functions attributed to the modules herein may be embodied as hardware, firmware, software, or any combination thereof. Depiction of different features as modules is intended to highlight different functional aspects and does not necessarily imply that such modules or units must be realized by separate hardware or software components. Rather, functionality associated with one or more modules may be performed by separate hardware or software components, or integrated within common or separate hardware or software components. Also, to the extent functionality may be implemented via software or firmware, such software or firmware is executed by a hardware processing unit, such as any of those described above, i.e., microprocessors, DSPs, or the like.

EM field emitter 106 generates an EM field around patient 102 (e.g., a portion of patient 102). In some examples, EM field emitter 106 may include three separate EM field generators that generate EM fields of different phases including signals in the 4-10 kHz range. Instrument sensor 110, located in surgical instrument 108, generates instrument location signals in response to the EM field generated by EM emitter 106. The instrument location signals may indicate a location (e.g., in three-dimensional space) of instrument sensor 110 in the EM field. Interface module 114 may determine a location of instrument sensor 110 in the EM field based on the instrument location signals generated by instrument sensor 110.

Reference sensor 111 may generate reference signals in response to the EM field generated by EM emitter 106. The reference signals may indicate a location of reference sensor 111 in the EM field. Interface module 114 may determine a location of reference sensor 111 based on the reference signals. Interface module 114 may also determine a location of instrument sensor 110 relative to reference sensor 111 based on the instrument location signals and the reference signals. The location of instrument sensor 110 relative to reference sensor 111 may be referred to as the "relative location" of instrument sensor 110.

After determining the relative location of instrument sensor 110, interface module 114 may map an instrument icon (e.g., crosshairs) onto the patient image that represents the location of instrument sensor 110 on or within the patient's anatomy. Interface module 114 may then display the instrument icon along with the patient image on display 116. In other words, interface module 114 may superimpose the instrument icon onto the patient image to indicate the location of instrument sensor 110 on or within patient 102.

Mapping the instrument icon onto the patient image may be referred to as a "registration process." The registration process may first include identifying the location of reference sensor 111 within the EM field. Then, the location of reference sensor 111 may be linked to a location on the patient image. For example, the clinician may input information into interface module 114 via user interface 118 that indicates the location of reference sensor 111 on the patient image. After the location of reference sensor 111 relative to the patient image is determined, interface module 114 may track the location of instrument sensor 110 relative to reference sensor 111 within the EM field, and then determine the location of instrument sensor 110 on the patient image relative to the location of reference sensor 111 on the patient image. Typically, reference sensor 111 is fixed externally to patient 102, or to a stationary object such as a table 120. Accordingly, reference sensor 111 may be relatively stationary during a procedure.

Figure 2:
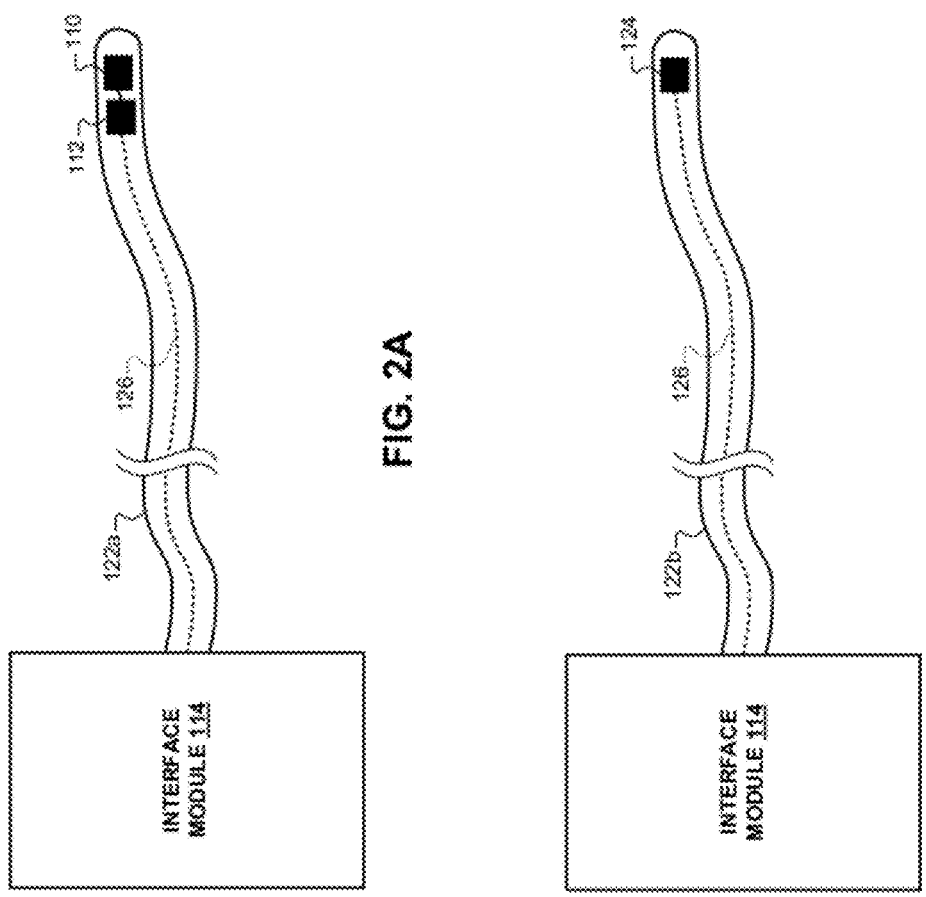
FIGS. 2A and 2B show example medical instruments that include different arrangements of instrument sensors and accelerometers.

As illustrated and described with respect to FIGS. 1 and 2A-2B, instrument 108 may be a catheter in some examples. Although instrument 108 is illustrated and described as a catheter device herein, instrument 108 may include devices other than catheters, and accordingly, instrument sensor 110 may be attached to and/or included within other instruments other than a catheter. For example, instrument 108 may include at least one of neural probes, leads including other sensors such as pressure, temperature, pH, or various biological detectors, catheters used to place stand-alone sensors, leads including micromanipulators, and various surgical tools or reference instruments. In general, instrument 108 may also include any instrument that may be inserted into a patient that may not be visually observed. Although a single instrument 108 is illustrated in surgical navigation system 100, surgical navigation system 100 may track the location of more than one instrument if more than one instrument in surgical navigation system 100 includes magnetic field sensors.

Instrument sensor 110 may generate various types of instrument location signals based on the type of sensor(s) included in instrument sensor 110. Instrument sensor 110 may generate instrument location signals that indicate location of instrument sensor 100 in one or more dimensions when instrument sensor 100 includes one or more axes. For example, instrument sensor 110 may generate instrument location signals that indicate the location of instrument sensor 100 in three-dimensional space. Accordingly, interface module 114 may determine the location of instrument sensor 110 within the EM field in terms of one or more dimensions. It may be assumed hereinafter that instrument sensor 110 generates instrument location signals that indicate the location of instrument sensor 110 in three-dimensional space, and accordingly, interface module 114 determines the location of instrument location sensor 110 in three-dimensional space.

Reference sensor 111 may generate various types of reference signals based on the type of sensor(s) included in reference sensor 111. Reference sensor 111 may generate reference signals that indicate the location of reference sensor 111 in one or more dimensions when reference sensor 111 includes one or more axes. For example, reference sensor 111 may generate reference signals that indicate the location of reference sensor 111 in three-dimensional space. Accordingly, interface module 114 may determine the location of reference sensor 111 within the EM field in terms of one or more dimensions. It may be assumed hereinafter that reference sensor 111 generates reference signals that indicate the location of reference sensor 111 in three-dimensional space, and accordingly, interface module 114 may determine the location of reference sensor 111 in three-dimensional space.

Based on the instrument location signals and reference signals from instrument sensor 110 and reference sensor 111, respectively, interface module 114 may determine the location of instrument sensor 110 relative to reference sensor 111 in three-dimensional space. For example, the relative location of instrument sensor 110 may, for example, be described by three coordinates, e.g., x, y, and z coordinates.

Instrument sensor 110 and reference sensor 111 may include various sensor technologies that enable sensing of the EM field and generation of instrument location signals and reference signals. Sensors 110, 111 may include, for example, any device that is suitable for generating a signal in response to an EM field. For example, sensors 110, 111 may each include, but are not limited to, normal magnetoresistance (NMR) sensors, anisotropic magnetoresistance (AMR) sensors, giant magnetoresistance (GMR) sensors, and Hall-effect sensors. In some examples, sensors 110, 111 may each include one or more of such sensors (e.g., NMR, AMR, GMR, Hall) that generate signals indicating a location of sensors 110, 111 in three dimensional space. Additionally, or alternatively, sensors 110, 111 may each include one or more wire-wound inductive sensors (e.g., orthogonal coils) for sensing one or more axes of data. Although any of the above sensors may be suitable for application in surgical navigation system 100, magnetoresistive sensors (e.g., GMR) and hall-effect sensors may be provided in smaller packages, provide more accurate readings of the EM field, and may be less expensive to produce than a wire-wound inductor based sensor.

Instrument 108 may include an accelerometer 112, or other motion sensor or inertial sensor, such as a gyroscopic sensor. Implementation of surgical navigation system 100 using an accelerometer 112 is discussed with reference to FIGS. 6-14. Implementation of surgical navigation system 100 including a gyroscopic sensor is discussed with respect to FIGS. 15-16. Accelerometer 112 may measure acceleration in one or more directions (e.g., along one or more axes). Accelerometer 112, as described hereinafter, includes three axes of measurement. Accordingly, accelerometer 112 may generate acceleration signals (e.g., voltage signals) that indicate an amount of acceleration experienced by accelerometer 112 along one or more axes of motion (e.g., x, y, z axes). As used herein, the axes/directions x, y, and z may indicate direction of acceleration in three-dimensional space, e.g., described by Cartesian coordinates formed by perpendicular x, y, and z axes.

Interface module 114 receives acceleration signals from accelerometer 112 and determines the amount of acceleration experienced by accelerometer 112 along the one or more axes measured by accelerometer 112. For example, interface module 114 may determine acceleration of accelerometer 112 in any of the x, y, and z-directions based on acceleration signals. Accordingly, interface module 114 may determine the amount of acceleration experienced by accelerometer 112 in any of the xy, yz, and xz, planes. Furthermore, interface module 114 may determine a single vector that represents the total amount of acceleration and direction of the acceleration experienced by accelerometer 112.

Accelerometer 112 and instrument sensor 110 may be positioned within proximity of one another on (or within) instrument 108. In some cases, accelerometer 112 and instrument sensor 110 may both be located, e.g., in the same package or on the same substrate. Since accelerometer 112 and instrument sensor 110 are arranged in close proximity to one another, accelerometer 112 and instrument sensor 110 may move together, and therefore experience the same, or roughly the same, acceleration. Therefore, acceleration signals generated by accelerometer 112 may indicate an amount of acceleration experienced by instrument sensor 110. Accordingly, interface module 114 may determine an amount of acceleration experienced by instrument sensor 110 based on acceleration signals received from accelerometer 112.

In some examples, instrument sensor 110 and accelerometer 112 may not be located in proximity to one another on instrument 108, but may be located a distance away from one another. For example, when instrument 108 is a rigid structure, instrument sensor 110 and accelerometer 112 may be separated from one another on instrument 108 and still experience the same acceleration.

FIGS. 2A and 2B show example instruments 122a, 122b, which in this example are illustrated as catheters (hereinafter "catheters 122a, 122b" or collectively "catheters 122"). Catheters 122 may include different arrangements of instrument sensor 110 and accelerometer 112. Catheters 122 may be catheters used for cardiac catheterization procedures, for example.

Catheter 122a of FIG. 2A includes instrument sensor 110 and accelerometer 112 in separate packages. In some examples, instrument sensor 110 may represent a wire-wound coil used to sense the EM field emitted by EM emitter 106. In other examples, instrument sensor 110 may represent a magnetoresistive sensor fabricated on a suitable substrate and included in a package separate from accelerometer 112. In other examples, an accelerometer and EM field sensor (e.g., wire-wound or magnetoresistive) may be included in the same package, illustrated as package 124 in FIG. 2B. In the example package 124 of FIG. 2B, instrument sensor 110 and accelerometer 112 may be fabricated on the same substrate or fabricated on different substrates and then packaged together (e.g., in a stacked die configuration). Inclusion of accelerometer 112 and instrument sensor 110 within the same package may ensure that acceleration experienced by both accelerometer 112 and instrument sensor 110 is equal.

Catheters 122 include electrical interconnects 126 that connect instrument sensor 110 and accelerometer 112 to interface module 114. For example, interface module 114 may provide power to instrument sensor 110 and accelerometer 112 via electrical interconnect 126. Additionally, instrument sensor 110 and accelerometer 112 may transmit data to interface module 114 via electrical interconnect 126.

In typical catheter applications, an instrument sensor may include a wire-wound inductor as the sensing element. Wire-wound inductors are typically interfaced to interface module 114 using connecting wires that extend within a catheter along the length of the catheter from the wire-wound inductor to interface module 114, illustrated as electrical interconnect 126. Due to the relatively long length of electrical interconnect 126, electrical interconnect 126 may pick up noise from the environment that may adversely affect measurements of the EM field. Noise picked up by electrical interconnect 126 may adversely affect the ability of interface module 114 to accurately determine the location of instrument sensor 110 in the EM field when instrument sensor 110 is a wire-wound inductor sensor.

In some examples, sensor 110, accelerometer 112, and/or package 124 may include signal conditioning circuitry that conditions transmitted signals in order to compensate for noise that may be picked up in electrical interconnect 126. The signal conditioning circuitry may condition signals transmitted from instrument sensor 110 and/or accelerometer 112 to interface module 114. The signal conditioning circuitry may be powered by interface module 114 via electrical interconnect 126. The signal conditioning circuitry may include, for example, amplification and filtering circuitry. Additionally, in some examples, the signal conditioning circuitry may include analog-to-digital conversion (ADC) circuits that convert acceleration signals and instrument location signals to digital data that may be transmitted along electrical interconnect 126 without significant distortion.

For example, providing signal conditioning circuitry near accelerometer 112 and instrument sensor 110, e.g., within the same package or on the same substrate, may increase the signal to noise ratio of signals received at interface module 114 relative to typical applications that include a wire-wound sensor. In some examples, signal conditioning circuitry may also be included in proximity to reference sensor 111.

Referring back to FIG. 1, in some examples, surgical navigation system 100 may include an optical navigation system (not shown), in addition to EM tracking, that tracks surgical instruments using infrared signals. For example, cameras of the optical navigation system may detect the position of moving instruments by triangulating their position with infrared signals. Interface module 114 may receives the signals from the cameras generate the position of the triangulated instruments on display 116.

Imaging device 104 acquires images of patient 102 which are subsequently processed by interface module 114 and displayed on display 106. As illustrated in FIG. 1, imaging device 104 includes a fluoroscopic imaging device mounted on a C-arm mount 128. Imaging device 104 may generate raw data that includes raw image data of patient 102 and position data generated by C-arm mount 128 that indicates a position of C-arm mount 128 while imaging device 104 acquired the raw image data. For example, position data generated by C-arm mount 128 may be used during the registration process in order to map the instrument icon on the patient image.

Although image device 104 is illustrated as a fluoroscopic imaging device mounted on a C-arm support, imaging device 104 may include other types of imaging devices. For example, imaging device 104 may include a magnetic resonance imaging (MRI) device, a computed tomography (CT) imaging device, or other suitable imaging device, e.g., that produces detailed structural landmarks. The raw image data generated by imaging device 104 in FIG. 1 includes fluoroscopic image data, although, in other examples, other raw image data may be collected when surgical navigation system 100 includes a different imaging device. For example, MRI image data may be acquired by an MR imaging device and CT data may be acquired by a CT imaging device.

Raw image data acquired from imaging device 104 may include two-dimensional or three dimensional data that may be processed by interface module 114 to generate a patient image on display 116. For example, imaging device 104 may produce a two-dimensional representation of patient anatomy on display 116 when raw image data includes two-dimensional data, and imaging device 104 may produce a three-dimensional representation of patient anatomy on display 116 when raw image data includes three-dimensional data.

Generally, interface module 114 may receive raw image data from imaging device 104, then process the raw image data in order to generate an image for display, then output the image to display 116 for a clinician to view. In some examples, interface module 114 may display an image on display 116 in real-time. Real-time image display may refer to acquisition and display of an image on display 116 with little or no delay. For example, delay may not be readily noticed by the clinician during real-time display. During real-time image display, interface module 114 may receive raw image data from imaging device 104, process the raw image data to generate an image for display, then output the image to display 116 for a clinician to view as the image data is being acquired. Accordingly, during real-time image display, a patient image may be displayed with only a minor delay from the time the raw image data is acquired by imaging device 104.

In other examples, an image may be displayed on display 116 in quasi real-time. Data displayed in quasi real-time on display 116 may not reflect the current status of patient 102, e.g., the location of internal organs of patient 102, but instead may be slightly delayed relative to real-time image display. For example, an image displayed in quasi real-time may be displayed on display 116 with a delay that is longer than the minor delay experienced during real-time display. The delay present in quasi real-time display of an image may arise due to the time required by imaging device 104 to acquire the image and the processing time used by interface module 114 to generate the image displayed on display 116. For example, in the case of three-dimensional fluoroscopic image processing, the delay may arise as the result of the imaging device acquiring multiple images and the processing steps used to generate the three-dimensional image, e.g., interface module 114 may stitch together the raw fluoroscopic image data to create a three-dimensional model on display 114.

In still other examples, data displayed on display 116 may be image data that was acquired further back in the past (e.g., on the order of days). For example, the image data displayed on display 116 may be retrieved from a storage device included in interface module 114 that includes images of patient 102 stored prior to the surgical navigation procedure. The storage device may store images of patient 102 that were acquired, e.g., by imaging device 104, before the surgical navigation procedure (e.g., within hours or days). Interface module 114 may retrieve the stored images from the storage device and display the stored images on display 116 during the surgical navigation procedure. In this example, interface module 114 may superimpose the instrument icon over the stored images.

Figure 3:
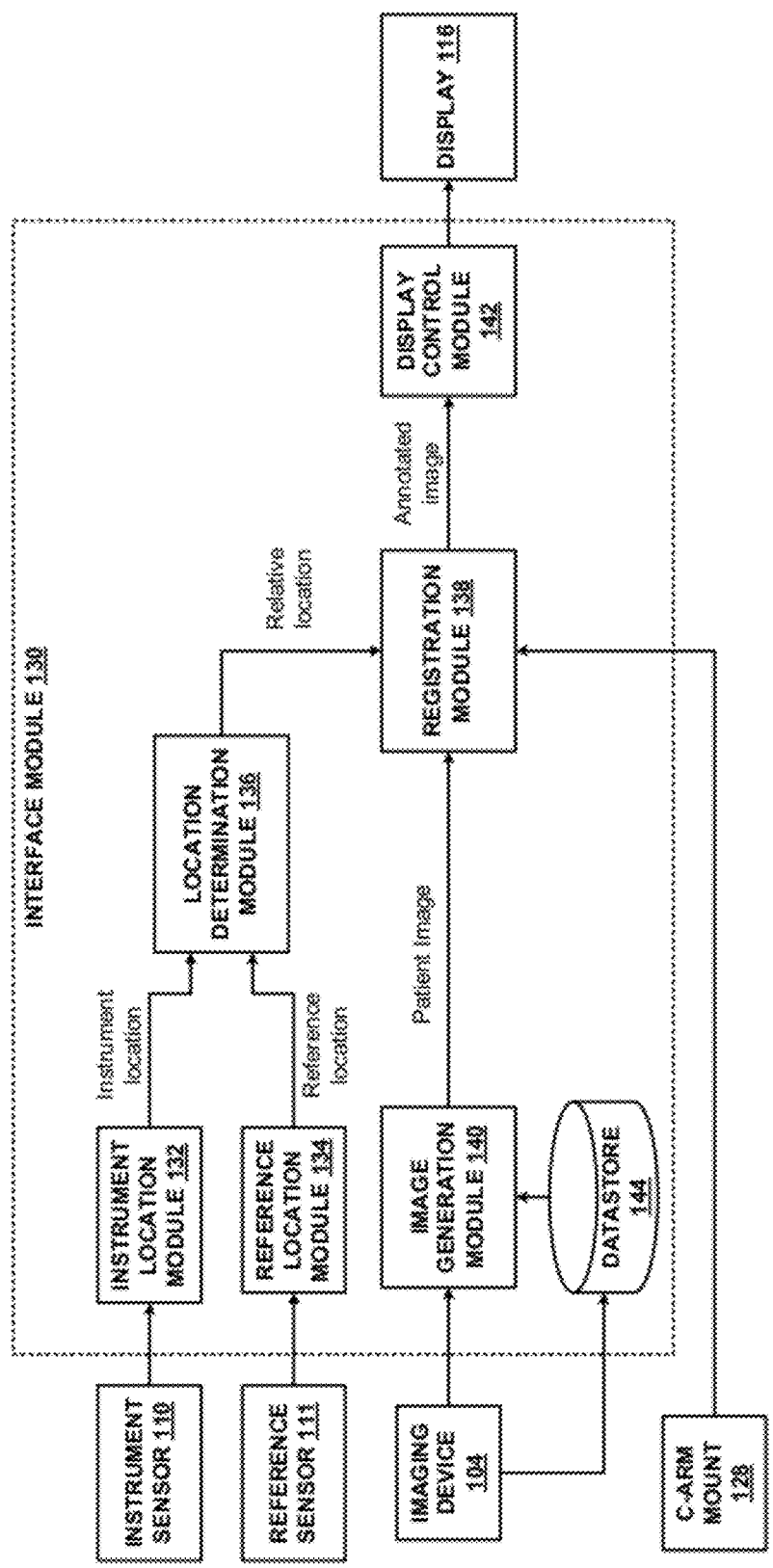
FIG. 3 shows an example interface module that does not include error correction functionality.

Referring now to FIG. 3, an example interface module 130 is illustrated in detail. Example interface module 130 of FIG. 3 illustrates the general functionality of modules included in interface module 114, but does not include error correction functionality according to the present disclosure. Interface module 114 of FIG. 1 that includes error correction functionality is described further with respect to FIGS. 6, 8, and 13.

Interface module 130 includes an instrument location module 132, a reference location module 134, and location determination module 136 that together may determine a relative location of instrument sensor 110. Interface module 130 includes a registration module 138 that generates an image that includes an instrument icon based on a patient image generated by image generation module 140 and the relative location of instrument sensor 110 received from location determination module 136. Display control module 142 outputs the generated image to display 116. Additionally, interface module 130 may include a datastore 144 that may store raw/processed image data acquired by imaging device 104.

Instrument location module 132 receives instrument location signals from instrument sensor 110. Instrument location module 132 determines a location of instrument sensor 110 within the EM field, generated by EM emitter 106, based on the instrument location signals. For example, instrument location module 132 may determine a location of instrument sensor 110 in three dimensional space (e.g., x, y, and z coordinates). As described above, in some examples, the instrument location signals received from instrument sensor 110 at interface module 130 may have been filtered and amplified, e.g., when additional circuitry is included with instrument sensor 110 in proximity to instrument sensor 110. If such additional circuitry (e.g., filters/amplifiers) is not included proximate to instrument sensor 110, instrument location module 132 may filter and amplify the instrument location signals to determine the location of instrument sensor 110. In some examples, the location of instrument sensor 110 may be expressed using three digital values that correspond to x, y, and z locations within the EM field.

Reference location module 134 receives reference signals from reference sensor 11. Reference location module 134 determines a location of reference sensor 11 within the EM field, generated by EM emitter 106, based on the reference signals. For example, reference location module 134 may determine the location of reference sensor 111 in three-dimensional space (e.g., x, y, and z coordinates). As described above, in some examples, reference signals received from reference sensor 111 at interface module 130 may have been filtered and amplified, e.g., when additional circuitry is included in proximity to reference sensor 111. If such additional circuitry (e.g., filters/amplifiers) is not included in proximity to reference sensor 111, reference location module 134 may filter and amplify the reference position signals to determine the location of reference sensor 111. In some examples, the location of reference sensor 111 may be expressed using three digital values, corresponding to x, y, and z locations within the EM field.

Image generation module 140 generates a patient image based on raw image data. Raw image data may include image data received from imaging device 104 and/or image data stored in datastore 144. The patient image generated by image generation module 140 may correspond to an image that is displayed on display 116, e.g., the image on display 116 that includes a superimposed instrument icon that represents a location of instrument sensor 110.

In some implementations, image generation module 140 may generate real-time images based on raw image data received from imaging device 104. For example, image generation module 140 may receive raw image data from imaging device 104 and immediately process the raw image data and generate a patient image for output to display 116. In other implementations, acquisition of raw image data by imaging device 104 and processing of raw image data by image generation module 140 may not occur as immediately as in the real-time scenario. In these implementations, image generation module 140 may generate a patient image for output to display 116 in a quasi real-time manner. In other words, the patient image generated by image generation module 140 may be delayed in time relative to when the image was acquired by imaging device 104.

In still other implementations, image generation module 140 may generate a patient image based on raw image data stored in and received from datastore 144. Image data used by image generation module 140 that was stored in datastore 144 may include raw image data gathered from a prior imaging of patient 102. For example, prior imaging of patient 102 may include a prior MRI or CT scan performed on patient 102, i.e., an MRI performed prior to the current surgical navigation procedure during which the patient image is displayed.

Location determination module 136 determines the location of instrument sensor 110 relative to reference sensor 111. The relative location of instrument sensor 110 may be expressed in terms of x, y, and z coordinates. For example, the x, y, and z coordinates of the relative location of instrument sensor 110 may indicate a distance between instrument sensor 110 and reference sensor 111 in the x, y, and z directions, respectively.

Figure 5B:
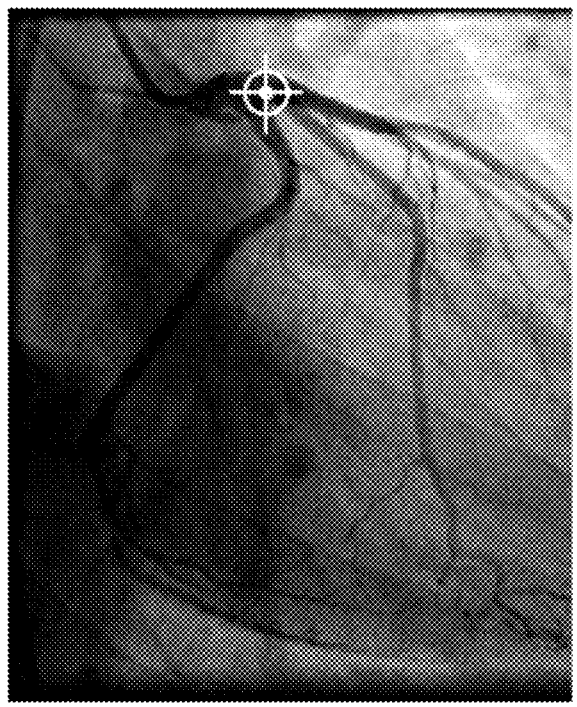
FIGS. 5A and 5B show example grayscale patient images having white crosshairs that are superimposed incorrectly and correctly, respectively.
Figure 5A:
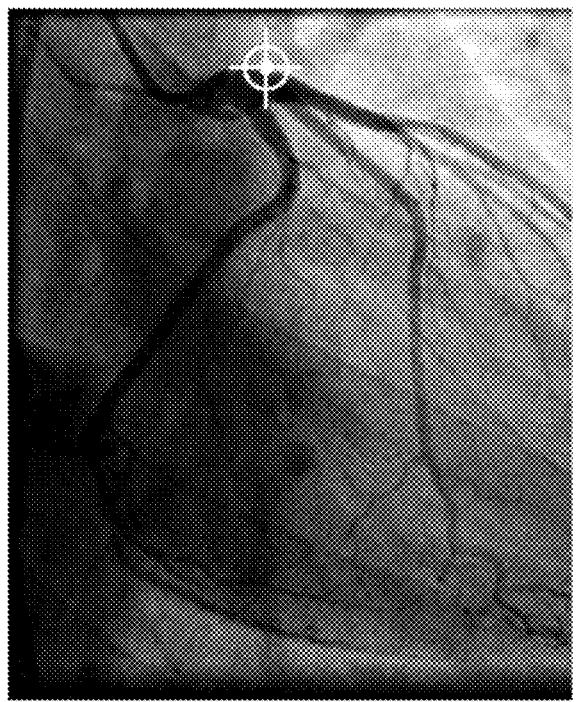

Registration module 138 performs a registration process based using the patient image and the relative location of instrument sensor 110. Additionally, registration module 138 may perform the registration process based on position data received from C-arm mount 128. During the registration process, registration module 138 superimposes an icon (e.g., crosshairs, or other icon), which represents instrument sensor 110 or the entire instrument 108, onto the patient image generated by image generation module 140. In some examples, registration module 138 may superimpose an instrument icon, as illustrated in FIGS. 5A-5B for example, on a patient image displayed in real-time. In other examples, registration module 138 may superimpose an instrument icon on a quasi real-time patient image. In still other examples, registration module 138 may superimpose an instrument icon on a still image. In any of these examples, either real-time or quasi real-time, the patient image may also include a two or three-dimensional model of patient 102, e.g., a computer model based on previously acquired raw image data.

Figure 4:
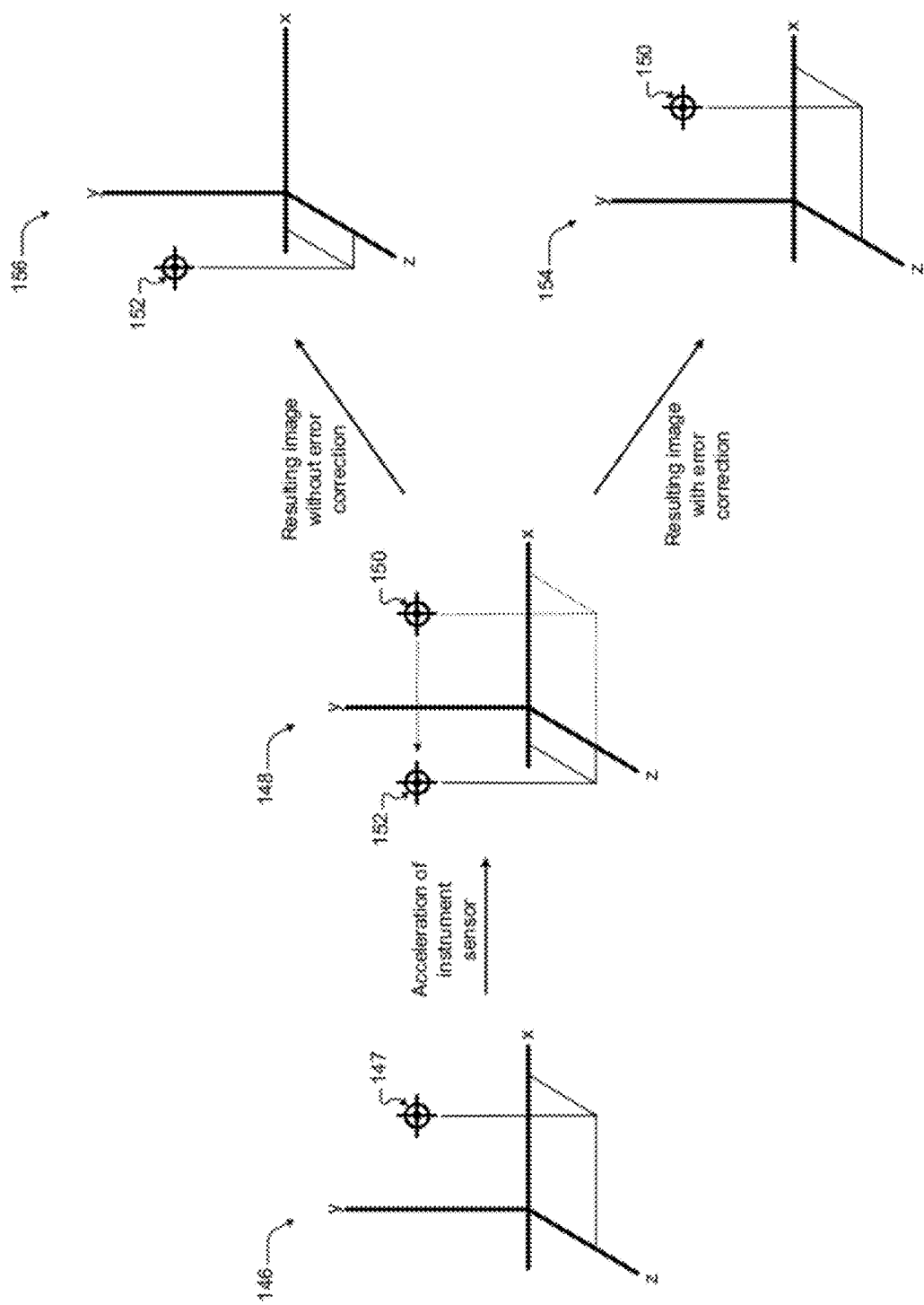
FIG. 4 shows example instances of error correction performed by an interface module that includes error correction functionality.

Registration module 138 may generate and superimpose a variety of different graphical representations of the instrument icon on the patient image. The instrument icon may be an icon that indicates the location of instrument sensor 110 or instrument 108 on the patient image displayed to a clinician on display 116. For example, the instrument icon displayed to a clinician may be a crosshair icon (as shown in FIGS. 4, 5A, and 5B) indicating a location of instrument sensor 110. In another example, instrument icon may be a graphical representation of instrument 108, e.g., a colored line that indicates the location of a length of a catheter including instrument sensor 110. Alternatively, or additionally, when instrument 108 is a catheter, the instrument icon may indicate a point at which a tip of the catheter is located. The location of the tip of the catheter may be determined by registration module 138 based on a known distance between the tip of the catheter and instrument sensor 110. In some examples, registration module 138 may generate and superimpose graphical representations of other areas of interest on the patient image. Other areas of interest may include multiple icons representing target locations for therapy (e.g., target drug injection sites), or icons representing areas to avoid with instrument 108.

A patient image that includes the superimposed instrument icon indicating the location of instrument 108 and/or instrument sensor 110 may be referred to hereinafter as an "annotated image." Accordingly, registration module 138 generates an annotated image based on at least one of the relative location of instrument sensor 110, the patient image, and the position of C-arm mount 128. Display control module 142 receives the annotated image and outputs the annotated image to display 116. For example, display control module 116 may output one or move views of the annotated image, including, but not limited to, a two dimensional side/top/bottom view and/or a three-dimensional view that may be adjusted by the clinician.

Under some circumstances, the relative location of instrument sensor 110 may be updated at a relatively greater rate than the patient image generated by image generation module 140. For example, the difference in rate may be due to the delay present when imaging device 104 acquires raw image data and/or the delay present when image generation module 140 generates the patient image from raw image data. In other words, due to this delay, the relative location of instrument sensor 110 may be updated at a relatively greater rate than the patient image upon which the relative sensor location is superimposed. Accordingly, a patient's anatomy displayed in the patient image may not be updated as fast as the superimposed instrument icon representing instrument sensor 110. In some examples, this may lead to an incorrect superimposition of the instrument icon onto the patient image.

In one example, a patient's heart may beat at a rate that is not accurately reproduced in the patient image displayed on display 116. In other words, the patient image may not be acquired or refreshed at a rate which allows for a smooth rendering of the real-time position of the patient's heart on display 116. In this example, a contraction of the heart may not be accurately represented in real-time on display 116, but the relative location of instrument sensor 110 within the EM field may be updated in real-time by location determination module 136. This may result in an incorrect mapping of the current relative location of instrument sensor 110 onto what is a delayed patient image. In other words, the instrument icon may not be superimposed on the patient image in the correct location because the patient image may not accurately represent the patient's current anatomy, while the relative location of instrument sensor 110 is determined accurately in real-time.

Surgical navigation system 100 of the present disclosure may identify instances when the instrument icon may not be superimposed correctly on the patient image. When such instances are recognized, surgical navigation system 100 may compensate for such errors. For example, the interface module 114 (e.g., of FIGS. 1, 6, 8, and 13) of surgical navigation system 100 may modify the relative location of instrument sensor 110 so that the instrument icon is accurately superimposed on the patient image.

In one example, interface module 114 may determine, based on an amount of acceleration of instrument sensor 110, when it is likely that the instrument icon may be superimposed incorrectly on the patient image. For example, when acceleration experienced by instrument sensor 110 is greater than a threshold acceleration, interface module 114 may reject, e.g., ignore, the location of instrument sensor 110 as determined by instrument location module 132 to prevent incorrect instrument location data from flowing through interface module 114, thereby preventing the instrument icon from being superimposed incorrectly onto the patient image for display to the clinician.

FIGS. 4 and 5 illustrate example instances of error correction performed by interface module 114 based on monitoring of an acceleration experienced by instrument sensor 110. Referring to FIG. 4, the crosshairs represent the instrument icon superimposed onto the patient image. The x, y, and z axes represent a three-dimensional patient image space. In other words, the x, y, and z axis represent coordinates of the patient image onto which the cross-hair icon is superimposed.

At 146, it may be assumed that the crosshairs 147 is superimposed at the correct location in the xyz image space. An acceleration, e.g., greater than the acceleration threshold, was experienced by instrument sensor 110 between the xyz axis illustrated and 146 and 148. For example, it may be assumed that the acceleration arose from a heartbeat that perturbed instrument sensor 110 but was not updated on the patient image. At 148, two crosshairs are illustrated. One crosshairs 150 indicates the location of the crosshairs prior to the acceleration, i.e., the position of the crosshairs that was correctly superimposed on the patient image. The other crosshairs 152 indicates where the crosshairs would be superimposed on the patient image (i.e., the image that has not been updated) after the acceleration based on the updated location of instrument sensor 110 as determined in real-time by instrument location module 132.

The crosshair 150 illustrated at 154, which hasn't moved since the acceleration was detected, is superimposed correctly on the image space since the location of the crosshair 150 has not been updated in the image space, just as the patient image has not been updated at 154 to reflect the heartbeat. The other crosshair 152 illustrated at 156 is superimposed incorrectly on the patient image since the location of crosshair 152 has been updated but the patient image has not yet been updated at 156.

FIG. 5A and FIG. 5B illustrate example grayscale patient images having white crosshairs that are superimposed incorrectly and correctly, respectively. The white crosshairs may indicate, for example, a location of instrument sensor 110 of a catheter. Accordingly, the patient images in FIGS. 5A and 5B may represent an annotated image displayed on display 116 during a cardiac catheterization procedure. In FIG. 5A, the white crosshair is located at the very edge of a vessel of the heart, indicating that the crosshair may be superimposed incorrectly onto the image, e.g., arising from motion of instrument sensor 110. FIG. 5B illustrates a correct superimposition of the instrument icon on the patient image, which may be due to, e.g., an error correction operation of the present disclosure that corrects for errors such as those present in FIG. 5A.

Figure 6:
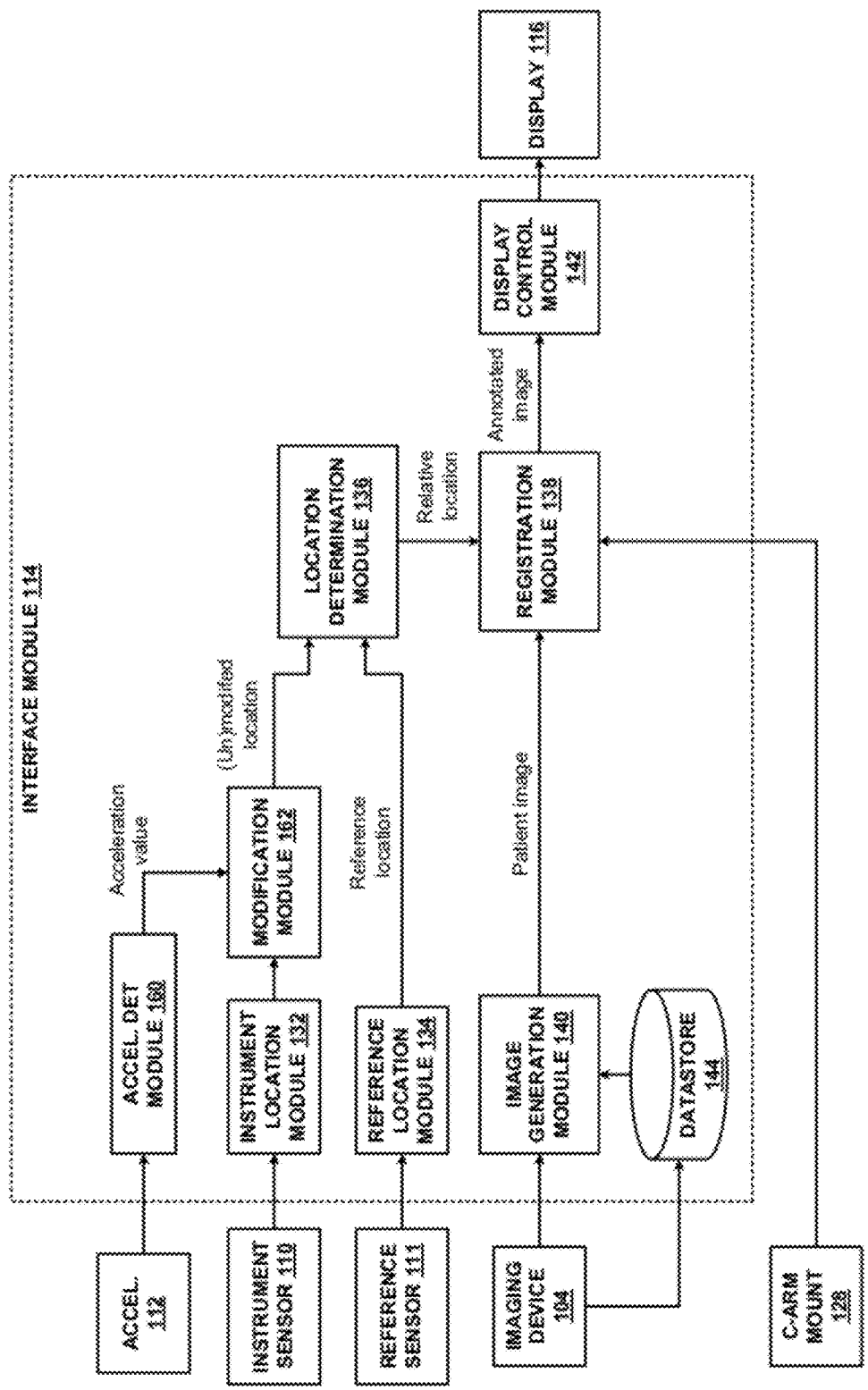
FIG. 6 shows an example interface module that includes error correction functionality that prevents errors when superimposing an instrument icon onto a patient image.

FIG. 6 shows an example interface module 114 that prevents errors when superimposing an instrument icon on a patient image. Interface module 114 includes an acceleration determination module 160 and a modification module 162 that prevent image registration errors due to motion of instrument sensor 110.

Acceleration determination module 160 is electrically coupled to accelerometer 112, and accordingly, acceleration determination module 160 may receive acceleration signals from accelerometer 112 and provide power to accelerometer 112. Acceleration determination module 160 receives acceleration signals from accelerometer 112 and determines an acceleration experienced by accelerometer 112 based on the acceleration signals. Hereinafter, the acceleration determined by acceleration determination module 160 may be referred to as an "acceleration value." For example, the acceleration value may indicate an amount of acceleration experienced by accelerometer 112 along one or more axes or a total acceleration experienced by accelerometer 112.

Since instrument sensor 110 may be placed in close proximity with, or mechanically attached to, accelerometer 112, instrument sensor 110 may move with accelerometer 112 and experience the same acceleration as accelerometer 112. Therefore, the acceleration signals generated by accelerometer 112 may indicate the acceleration experienced by instrument sensor 110, and the acceleration value determined by acceleration determination module 160 may indicate the acceleration of instrument sensor 110. Thus, acceleration determination module 160 may determine an amount of acceleration experienced by instrument sensor 110 along one or more axes (e.g., x, y, and z directions). Additionally, or alternatively, acceleration determination module 160 may determine a total acceleration of instrument sensor 110, e.g., a value that represents the magnitude and direction of the acceleration of instrument sensor 110.

Modification module 162 may generate modified or unmodified location values based on the acceleration value determined by acceleration determination module 160 and based on one or more locations determined by instrument location module 132. The unmodified location value may be equal to the location of instrument sensor 110 as determined by instrument location module 132. In other words, modification module 162 may generate the unmodified location value by allowing the location of instrument sensor 110, as determined by instrument location module 132, to pass through modification module 162 unchanged. The modified location value determined by modification module 162 may be different from the location of instrument sensor 110 determined by instrument location module 132. Modification module 162 may generate the modified location value using a variety of techniques described hereinafter. In some implementations, modification module 162 may generate the modified location value in response to an acceleration value that is greater than a threshold value, as described with respect to FIG. 8, for example. In other implementations, modification module 162 may generate the modified location value based on frequency domain analysis of stored acceleration values, as described with respect to FIG. 13, for example. For example, modification module 162 may perform a frequency domain analysis on acceleration values to identify frequency components of the acceleration values that may cause the instrument icon to be superimposed incorrectly on the patient image, then generate modified location values to compensate for such components if present.

In general, modification module 162 may generate an unmodified location value when little or no acceleration is experienced by instrument sensor 110. In other words, modification module 162 may generate an unmodified location value when instrument sensor 110 is experiencing less than a threshold amount of acceleration. However, when a threshold acceleration is experienced by instrument sensor 110, modification module 162 may generate a modified location value that is different than the location of instrument sensor 110 as determined by instrument location module 132. For example, the threshold acceleration may be based on an amount of acceleration that may cause error during the registration process and result in an incorrect mapping of the instrument icon onto the patient image. The threshold acceleration may vary depending on the surgical navigation procedure, e.g., the rate at which images are acquired by imaging device 104. For example, when surgical navigation system 100 includes an imaging device 104 that acquires images at a slower rate, the acceleration threshold may be lowered in order to reject errors caused by smaller accelerations that may likely have an adverse affect on mapping of the instrument icon onto the slowly acquired image.

In some examples, the threshold acceleration may be based on an amount of acceleration that indicates that movement of instrument sensor 110 was not intended by the clinician, but instead caused by a disturbance. For example, in the case where instrument sensor 110 is in a catheter, an acceleration imposed on the catheter by a clinician, e.g., when moving the catheter during the procedure, may be less than an acceleration that is imposed on instrument sensor 110 by a heartbeat. Accordingly, in this scenario, the acceleration threshold may be selected to be greater than a predicted motion by the clinician, but less than an acceleration imposed by a heartbeat, so modification module 162 may generate a modified location value that removes motion of instrument sensor 110 due to a heartbeat, but not due to motion by the clinician.

Location determination module 136 determines the relative location of instrument sensor 110 based on the reference location and either the unmodified location value or the modified location value, depending on which is received. Registration module 138 then registers the relative location of instrument sensor 110 on the patient image to generate the annotated image. The annotated image is then output to display 116 by display control module 116.

Figure 7:
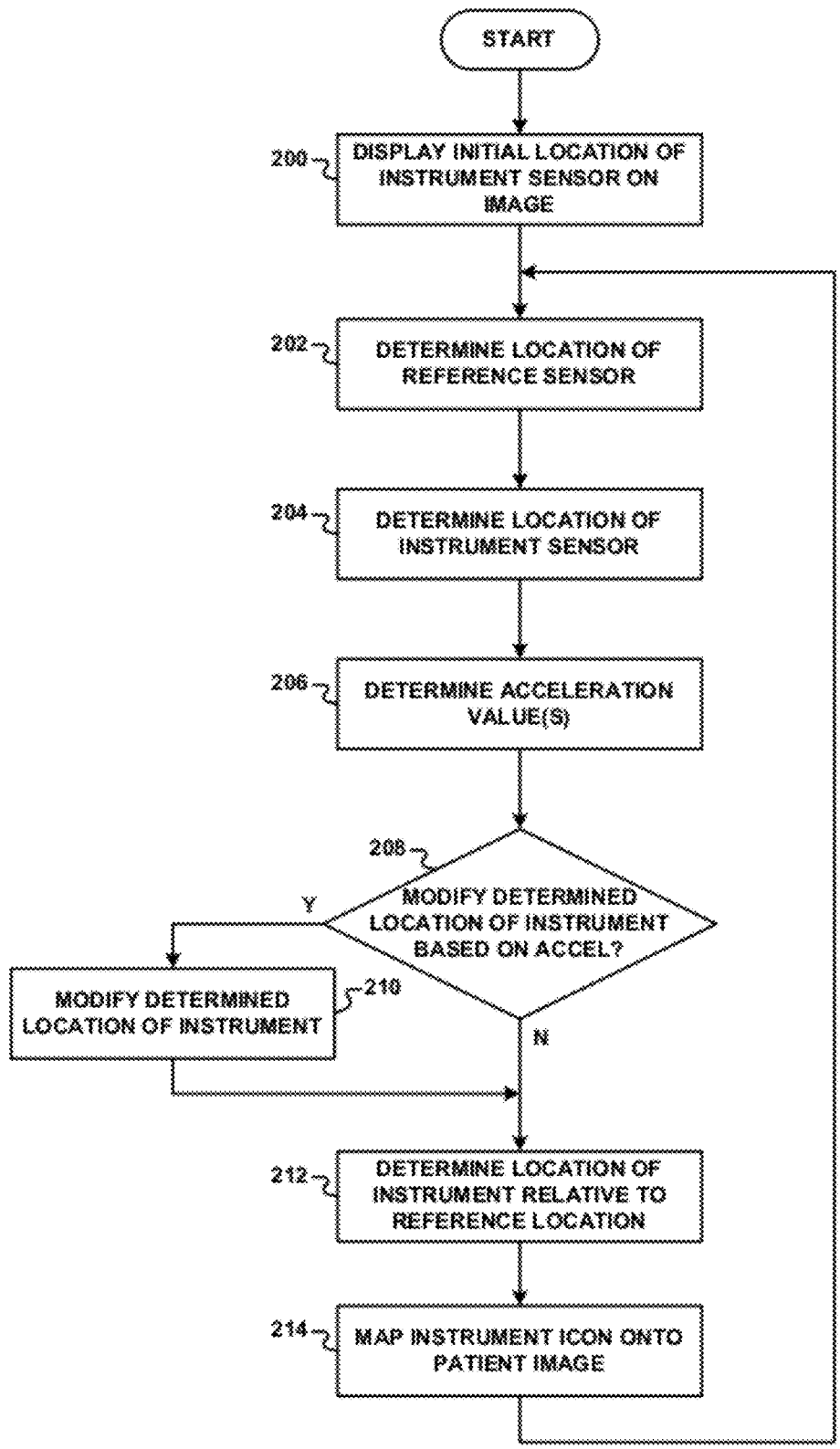
FIG. 7 shows an example error correction method.

FIG. 7 shows an example error correction method. For illustration purposes, it is assumed that the method begins during a time when instrument sensor 110 is not experiencing an acceleration that may cause an error in mapping of the instrument icon onto the patient image. Initially, modification module 162 generates an unmodified location value, and accordingly, the annotated image output by display control module 142 may illustrate the instrument icon in the correct location relative to the patient image (200).

Reference location module 134 determines the location of reference sensor 111 based on reference signals received from reference sensor 111 (202). Instrument location module 132 determines the location of instrument sensor 110 based on instrument location signals received from instrument sensor 110 (204). Acceleration determination module 160 determines one or more acceleration values based on acceleration signals received from accelerometer 112 (206).

Modification module 162 then determines whether to generate a modified location value or an unmodified location value based on the one or more acceleration values (208). In some examples, modification module 162 may generate the modified location value when the one or more acceleration values indicate that instrument sensor 110 is experiencing an acceleration that is greater than an acceleration threshold. In these examples, modification module 162 may generate an unmodified location value when the acceleration values indicate that instrument sensor 110 is experiencing an acceleration that is less than the threshold acceleration.

If modification module 162 decides to generate a modified location value, modification module 162 performs one or more modification operations to generate the modified location value (210). Example modification operations are described hereinafter with respect to FIGS. 8-14. If modification module 162 decides to generate an unmodified location value, modification module 162 may not modify the instrument location as determined by instrument location module 132, but instead may allow the instrument location to "pass through" to location determination module 136 as an unmodified location value.

Location determination module 136 determines the relative location of instrument sensor 110 based on the reference location and either the modified location value determined in block (210) or the unmodified location value (212). Registration module 138 maps the relative location on the patient image generated by image generation module 140 to generate an annotated image which is output to display via display control module 142 (214).

Figure 8:
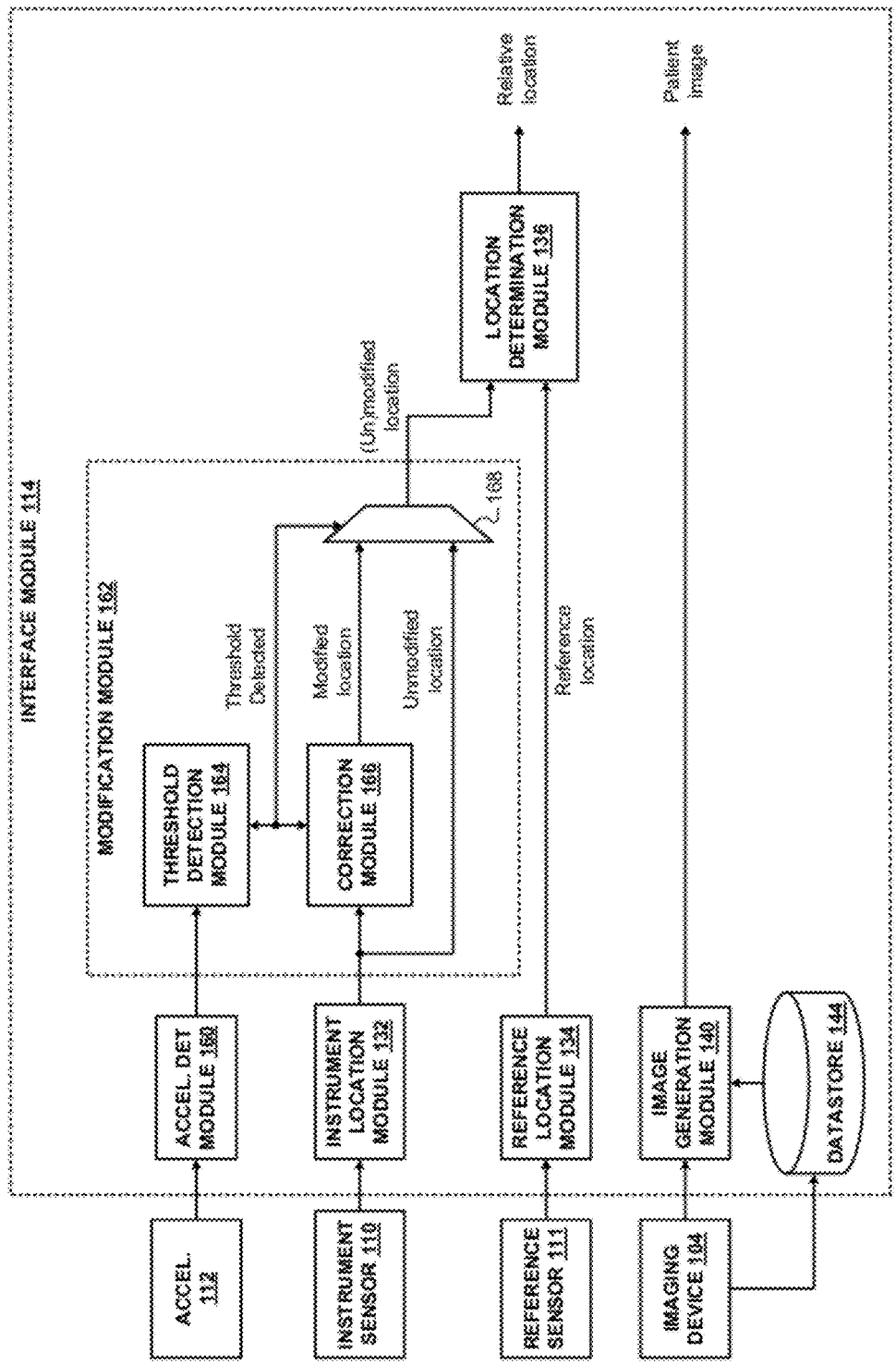
FIG. 8 shows a portion of an interface module that includes a threshold detection module, a correction module, and a selection module.

FIG. 8 shows a portion of interface module 114 that includes an example modification module 162. Modification module 162 includes a threshold detection module 164, a correction module 166, and a selection module 168. Operation of threshold detection module 164, correction module 166, and selection module 168 are described with reference to FIGS. 9A, 9B, 10, 11A, 11B, and 12.

Threshold detection module 164 monitors acceleration values received from acceleration determination module 160. Threshold detection module 164 determines when an acceleration value is greater than the threshold acceleration, and then indicates to correction module 166 and selection module 168 when the acceleration value is greater than the threshold acceleration. Additionally, threshold detection module 164 may indicate to correction module 166 and selection module 168 when an acceleration value is not greater than (i.e., less than or equal to) the threshold acceleration.

Correction module 166 receives the instrument location from instrument location module 132. Correction module 166 determines a modified location value when threshold detection module 164 indicates that the acceleration value is greater than the threshold acceleration. Selection module 168 connects one of the correction module 166 (i.e., the modified location value) and the instrument location module 132 (i.e., the unmodified location value) to location determination module 136. In other words, selection module 168 selects which of the modified location value and the unmodified location value is used by location determination module 136 to determine the relative location of instrument sensor 110. Selection module 168 selects the modified location value for use at location determination module 136 when threshold detection module 164 indicates that the acceleration value is greater than the threshold acceleration. Selection module 168 selects the unmodified location value for use by location determination module 136 when threshold detection module 164 indicates that the acceleration value is less or equal to the threshold acceleration.

During periods when the acceleration value is less than the acceleration threshold, as indicated by threshold detection module 164, selection module 168 selects the unmodified location value for input to location determination module 136. Accordingly, during periods when the acceleration value is less than or equal to the threshold acceleration, location determination module 136 determines the relative location of instrument sensor 110 based on the unmodified location value.

Correction module 166 may determine the modified location value when the acceleration value exceeds (i.e., is greater than) the threshold acceleration. As used hereinafter, the threshold acceleration may refer to a magnitude of acceleration experienced by instrument sensor 110, independent of direction. For example, the threshold acceleration may have a positive value, indicating an acceleration experienced in a first direction, or may have a negative value indicating that the acceleration is in a direction opposite to the first direction. Accordingly, an acceleration that is greater than the threshold acceleration may indicate that the acceleration is a larger positive acceleration than a positive threshold acceleration or a larger negative acceleration than a negative threshold acceleration. Thus, in one example, acceleration of instrument sensor 110 may reach or exceed the acceleration threshold when an acceleration experienced by instrument sensor 110 transitions from an acceleration that is less than the threshold acceleration to an acceleration that is greater than the threshold acceleration.

In some examples, the threshold acceleration may include a single threshold value. For example, the single threshold value may be reached when the total magnitude of acceleration experienced by instrument sensor 110 (e.g., in the x, y, and z directions) is greater than the single threshold acceleration. In another example, the single threshold value may indicate a threshold along a single axis and therefore the single acceleration threshold may be reached when acceleration along a single axis of instrument sensor 110 is greater than the single threshold value.

Correction module 166 may generate the modified location value in various ways. In one example, when correction module 166 receives indication that the acceleration value is greater than the threshold acceleration, correction module 166 may set the modified location value equal to the instrument location at the time the acceleration value reached the threshold acceleration. In other words, correction module 166 may store the location of instrument sensor 110 when the acceleration value reaches the threshold acceleration, and correction module 166 may then continue to output the stored value as the modified location value although the location determined by instrument location module 132 may be varying. In this manner, a positional change of instrument sensor 110 may be prevented from affecting the relative location of instrument sensor 110 mapped onto the patient image during periods when instrument sensor 110 is experiencing elevated levels of acceleration that may cause error in mapping the instrument icon onto the patient image.

Correction module 166 may output the stored value for a predetermined period of time in response to the acceleration value reaching the threshold acceleration. Additionally, selection module 168 may select the modified location value for output to location determination module 136 for the predetermined period of time in response to the acceleration value reaching the threshold acceleration. Accordingly, for a predetermined period of time after the acceleration reaches the acceleration threshold, location determination module 136 may determine the relative location of instrument sensor 110 based on the modified location value. After the predetermined period of time, selection module 168 may select the unmodified location value for output to location determination module 136, and location determination module 136 may determine the relative location of instrument sensor 110 based on the unmodified location value until the acceleration once again increases beyond the threshold acceleration.

Figure 9A:
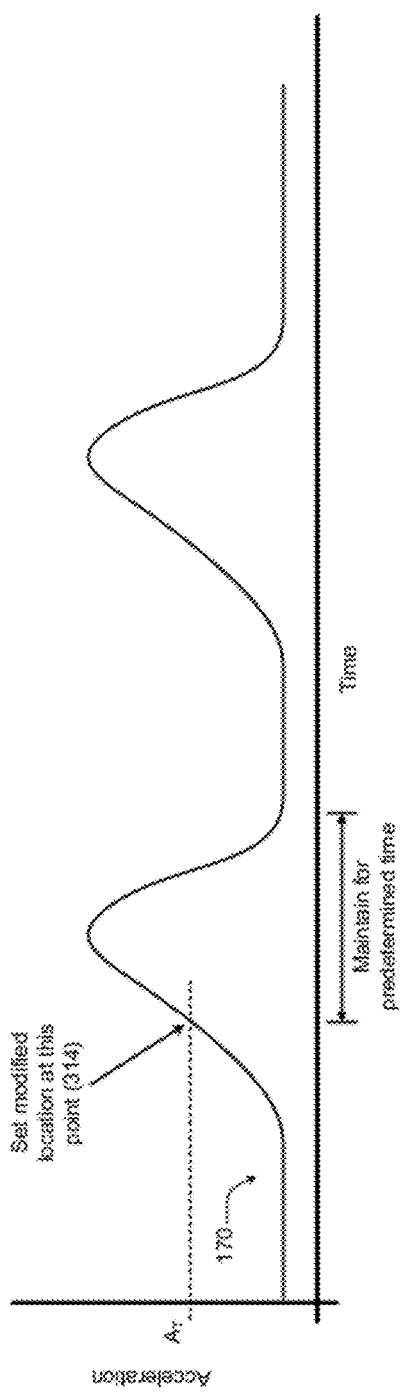
FIGS. 9A and 9B illustrate example acceleration curve traces versus time as received by the threshold detection module of FIG. 8.
Figure 9B:
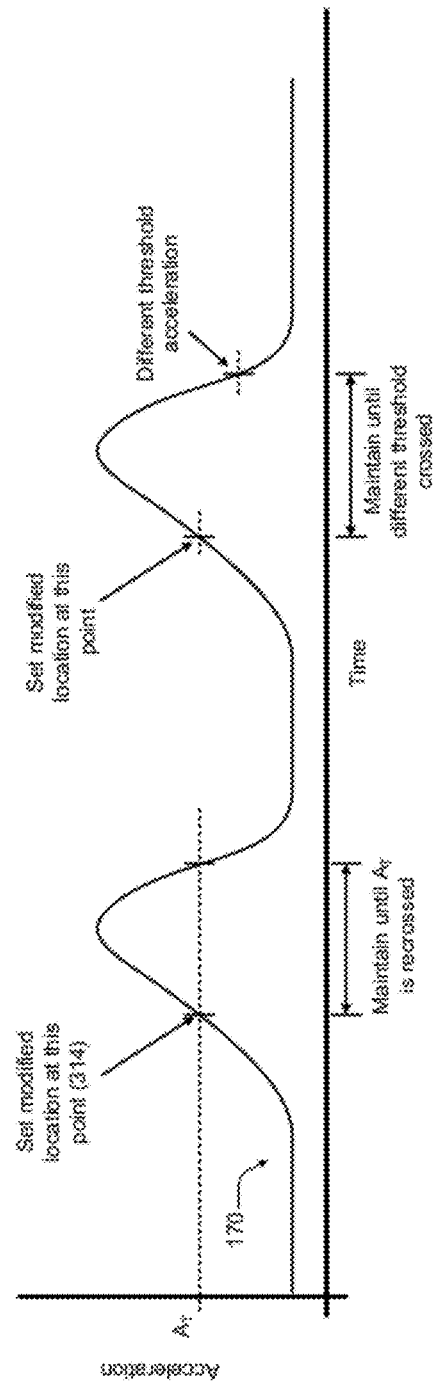
Figure 10:
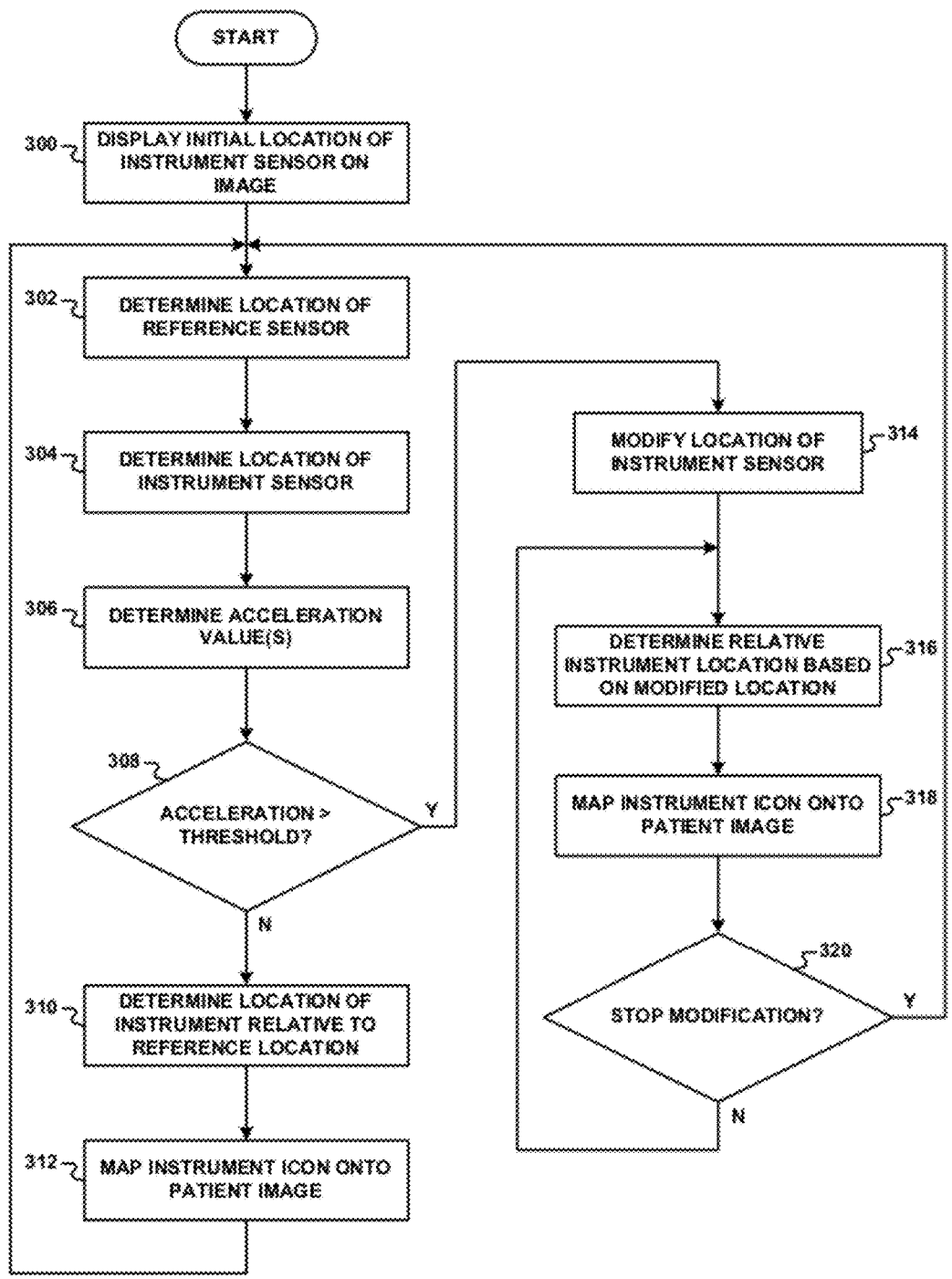
FIG. 10 shows an example error correction method using the threshold detection module, correction module, and selection module of FIG. 8.

FIG. 10, with reference to FIGS. 9A-9B, describes an example error correction method using threshold detection module 164, correction module 166, and selection module 168 of FIG. 8. FIGS. 9A-9B illustrate an example acceleration curve trace versus time as received by threshold detection module 164. The threshold acceleration is indicated as $A_T$.

For illustration purposes, it is assumed that the method begins during a time when instrument sensor 110 is not experiencing an acceleration that is greater than the threshold acceleration, e.g., illustrated at 170. Initially, modification module 162 generates an unmodified instrument location, and accordingly, the annotated image output to display 116 may illustrate the instrument icon in the correct location relative to the patient image (300).

Reference location module 134 determines the location of reference sensor 111 based on reference signals received from reference sensor 111 (302). Instrument location module 132 determines the location of instrument sensor 110 based on instrument location signals received from instrument sensor 110 (304). Acceleration determination module 160 determines one or more acceleration values based on acceleration signals received from accelerometer 112 (306).

Modification module 162 then determines whether to generate a modified or unmodified location value based on the one or more acceleration values (308). If threshold detection module 164 determines that the acceleration value is less than or equal to the threshold acceleration (as illustrated at 170 in FIGS. 9A-9B), selection module 168 selects the unmodified location value, i.e., the output of instrument location module 132. Location determination module 136 then determines the relative location of instrument sensor 110 based on the unmodified location value (310) and registration module 138 maps the instrument icon onto the patient image (312). The annotated image is then displayed on display 116.

If threshold detection module 164 determines that the acceleration value is greater than the threshold acceleration, then correction module 166 stores the instrument location at the time the acceleration reached the threshold acceleration and then sets the modified location equal to this stored value (314). Additionally, selection module 168 selects the modified location value for output to location determination module 136.

Location determination module 136 then determines the relative location of instrument sensor 110 based on the modified location value (316) and registration module 138 generates the annotated image based on this relative instrument location (318). Correction module 166 and selection module 168 then decide whether to stop outputting the modified location value to location determination module 136 (320).

In one example, correction module 166 and selection module 168 may operate to output the modified location value (e.g., the stored value) to location determination module 136 for a predetermined amount of time, as illustrated in FIG. 9A. In this example, selection module 168 may stop outputting the modified location value and switch to the unmodified location value after expiration of the predetermined amount of time, returning to block (302). Furthermore, in this example, until the predetermined amount of time has passed, correction module 166 and selection module 168 may continue to output the modified location value to location determination module 136.

In another example, at block (320), correction module 166 and selection module 168 may determine whether to output the modified location (e.g., the stored value) based on the current acceleration value as determined by acceleration determination module 160. In one example, selection module 168 may output the modified location value until threshold detection module 164 detects that the acceleration experienced by accelerometer 112 has decreased to a value less than the threshold acceleration, as illustrated in FIG. 9B. Selection module 168 may then select the unmodified location value for output to location determination module 136. Instead of switching to the unmodified location value upon re-crossing the same threshold acceleration, in some examples, selection module 168 may select the unmodified location value when the acceleration re-crosses another value of acceleration (e.g. greater than or less than the threshold acceleration). This is also illustrated in FIG. 9B.

Figure 12:
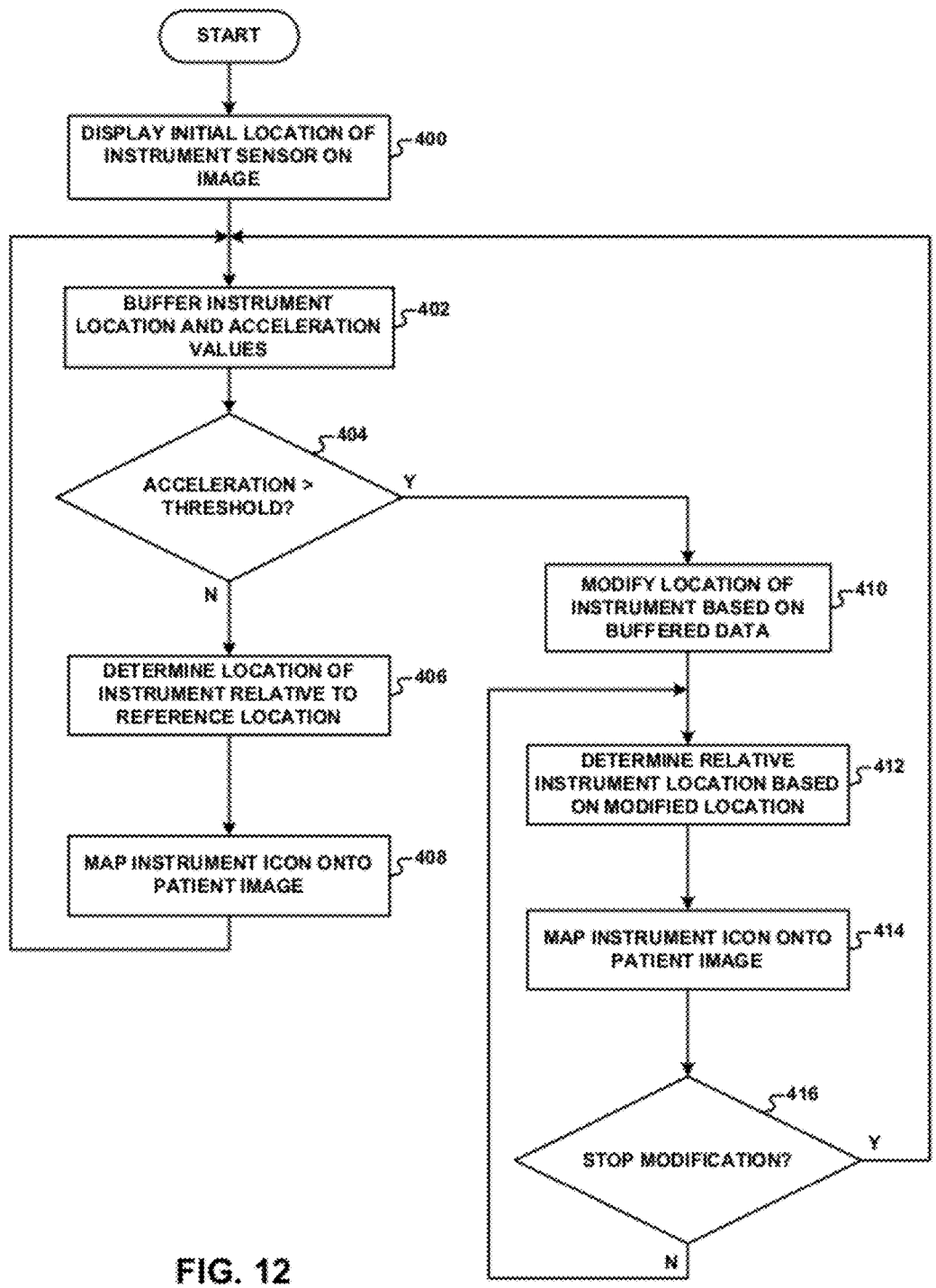
FIG. 12 illustrates another error correction method using the threshold detection module, correction module, and selection module of FIG. 8.

FIGS. 11A, 11B, and 12 illustrate another method for error correction using modification module 168 of FIG. 8. In the method illustrated in FIG. 12, instead of choosing the instrument location that occurs at the time the acceleration value crosses the threshold acceleration, correction module 166 may choose a previously stored instrument location value from a buffer that continuously stores instrument location values. The buffer may be included in correction module 166. For illustration purposes, it is assumed that the method of FIG. 12 begins during a time when instrument sensor 110 is not experiencing an acceleration that is greater than the threshold acceleration, illustrated at 170. Initially, modification module 162 determines an unmodified location value, and accordingly, the annotated image output to display 116 may illustrate the instrument icon in the correct location relative to the patient image (400).

In the example method of FIG. 12, threshold detection module 164 may continuously store acceleration values in a buffer included in threshold detection module 164 and correction module 166 may continuously store instrument location values in a buffer included in correction module 166 (402).

Modification module 162 then determines whether to generate a modified or unmodified location value based on one or more buffered acceleration values (404). If threshold detection module 164 determines that the acceleration value is less than or equal to the threshold acceleration (as illustrated at 170 in FIGS. 11A and 11B), selection module 168 selects the unmodified location value, i.e., the output of instrument location module 132. Location determination module 136 then determines the relative location of instrument sensor 110 based on the unmodified location (406) and registration module 138 maps the instrument icon onto the patient image (408).

If threshold detection module 164 determines that the acceleration value is greater than the threshold acceleration, then correction module 166 selects a stored value of the instrument location from the buffer (e.g., within correction module 166) for output as the modified location value (410). Additionally, selection module 168 selects the modified location value for output to location determination module 136. Correction module 166 may select the stored value of the instrument location from the buffer in a variety of ways.

In some implementations, correction module 166 may select the stored value by selecting a value from the buffer that corresponds to an acceleration value that was not greater than the threshold acceleration. In other words, correction module 166 may select a buffered instrument location value that was sampled at approximately the same time as an acceleration value that was not greater than the threshold acceleration. For example, correction module 166 may first identify a buffered acceleration value (e.g., from the buffer in threshold detection module 164) that was less than the threshold acceleration. Correction module 166 may then select an instrument location value that was buffered (i.e., occurred) at the same time, or approximately the same time, as the selected acceleration value. Correction module 166 may then output the selected instrument location value as the modified location value in order to return the relative instrument location (determined by location determination module 136) to an appropriate location that is untainted by the undesirable acceleration that is currently being experienced by instrument sensor 110.

In other implementations, correction module 166 may select the stored instrument location value by selecting a sampled location value from the buffer which was sampled a predetermined amount of time before the acceleration value was greater than the threshold acceleration. The predetermined amount of time may, for example, correspond to a predetermined number of samples of the location value in the buffer. Selection of an instrument location value a predetermined amount of time before occurrence of the acceleration value that was greater than the threshold value may serve to eliminate motion of instrument sensor 110 due to undesirable acceleration. In other words, setting the instrument location value to a value that occurs just previous to the acceleration reaching the threshold acceleration may eliminate the positional change of instrument sensor 110 due to the undesirable acceleration, and therefore prevent the positional change due to the undesirable acceleration from being mapped onto the patient image.

The predetermined amount of time may be based on the rate at which the acceleration may change. For example, during a surgical navigation procedure in which it is anticipated that acceleration may change rapidly, the predetermined period of time may be selected to be relatively short since the undesirable acceleration may occur more abruptly. During a procedure in which the undesirable acceleration is likely to be more prolonged (e.g., instead of abrupt), a longer predetermined time may be selected to ensure that an instrument location value is selected that is unaffected by the acceleration.

After correction module 166 selects the stored value of the instrument location from the buffer and selection module 168 selects the modified location for output to location determination module 136 (410), location determination module 136 determines the relative location of instrument sensor 110 based on the modified location value (412) and registration module 138 generates the annotated image based on this relative location (414). Correction module 166 and selection module 168 then decide whether to stop outputting the modified location value to location determination module 136 (416). In one example, correction module 166 and selection module 168 may operate to output the modified location value (e.g., the value retrieved from the buffer) to location determination module 136 for a predetermined amount of time. In this example, selection module 168 may stop outputting the modified location value and switch to the unmodified location value after expiration of the predetermined amount of time, returning to block (402). This is illustrated in FIG. 11A. Furthermore, in this example, until the predetermined amount of time has passed, correction module 166 and selection module 168 may continue to output the modified location value to location determination module 136.

In another example, at block (416), correction module 166 and selection module 168 may determine whether to output the modified location value (e.g., the stored value) based on the current acceleration value as determined by acceleration determination module 160. In one example, selection module 168 may output the modified location value until threshold detection module 164 detects that the acceleration experienced by accelerometer 112 has decreased to a value less than the threshold acceleration, as illustrated in FIG. 11B. Selection module 168 may then select the unmodified location value for output to location determination module 136. Instead of switching to the unmodified location value upon re-crossing the same threshold acceleration, in some examples, selection module 168 may select the unmodified location value when the acceleration re-crosses another value of acceleration (e.g., greater than or less than the threshold acceleration). This is illustrated in FIG. 11B.

Figure 13:
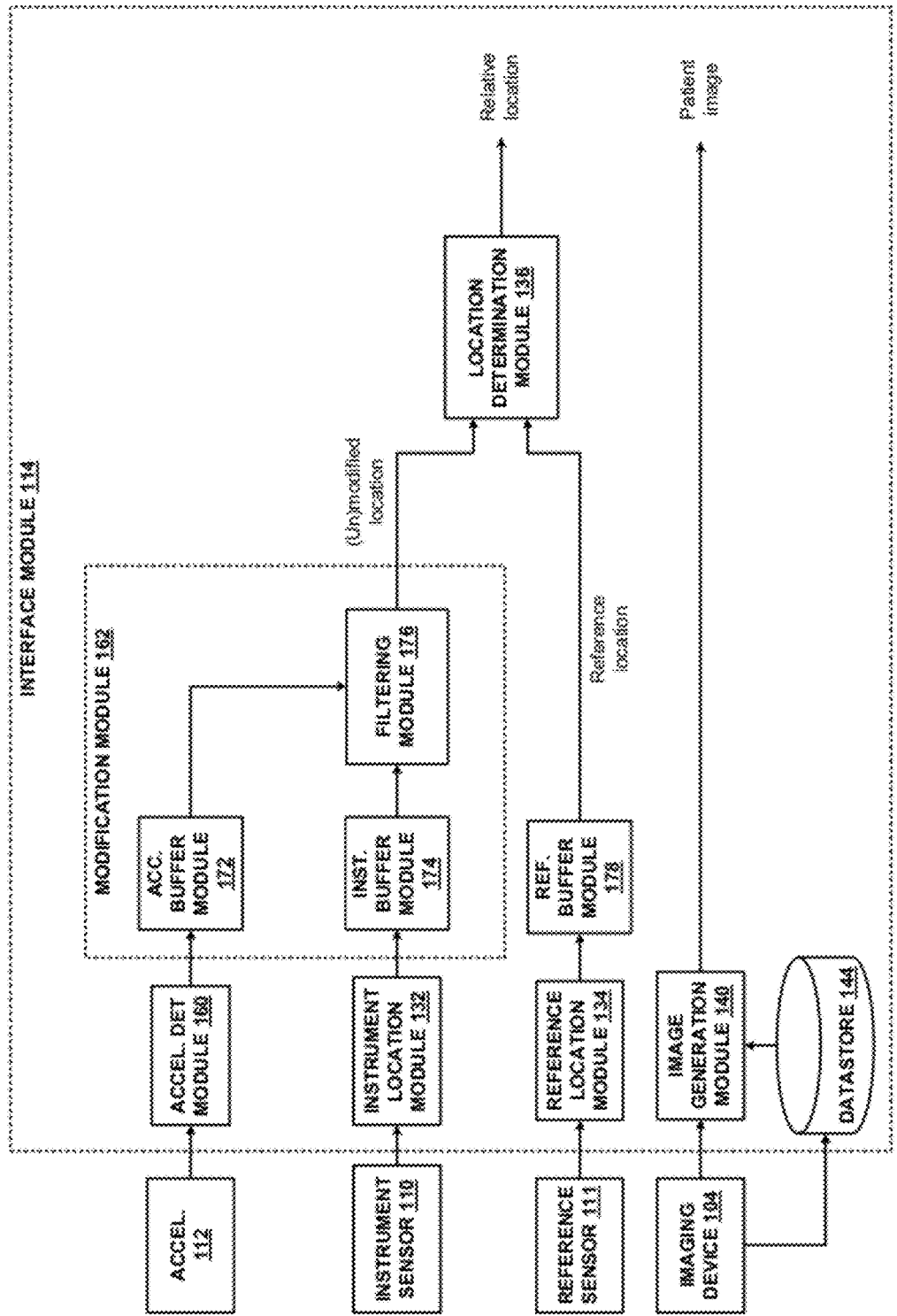
FIG. 13 shows another example interface module that provides error correction functionality using a frequency domain analysis of stored acceleration values.

FIG. 13 illustrates an alternative modification module 162 that may be included in an alternative interface module 114. Modification module 162 includes an acceleration buffer module 172, an instrument buffer module 174, and a filtering module 176. Additionally, interface module 114 includes a reference buffer module 178.

Acceleration buffer module 172 stores acceleration values received from acceleration determination module 160. For example, acceleration buffer module 172 may store a predetermined number of acceleration values received from acceleration determination module 160. Acceleration values which are most recently received at acceleration buffer module 172 may replace acceleration values that have been stored in acceleration buffer module 172 for the longest amount of time. For example, acceleration buffer module 172 may include a first in, first out (FIFO) buffer.

Instrument buffer module 174 stores instrument location values received from instrument location module 132. For example, instrument buffer module 174 may store a predetermined number of instrument location values received from instrument location module 132. Instrument location values which are most recently received at instrument buffer module 174 may replace instrument location values that have been stored in instrument location buffer for the longest amount of time. For example, instrument buffer module 174 may include a FIFO buffer.

Reference buffer module 178 stores reference location values received from reference location module 134. For example, reference buffer module 178 may store a predetermined number of reference location values received from reference location module 134. Reference location values which are most recently received at reference buffer module 178 may replace reference location values that have been stored in reference buffer module 178 for the longest amount of time. For example, reference buffer module 178 may include a FIFO buffer.

Filtering module 176 receives acceleration values from acceleration buffer module 172 and instrument location values from instrument buffer module 174. Filtering module 176 may modify (i.e., adjust) instrument location values received from instrument buffer module 174 based on acceleration values received from acceleration buffer module 172. In general, filtering module 176 may perform analysis on a set of acceleration values buffered in acceleration buffer module 172 and then adjust the instrument location values received from instrument buffer module 174 based on the analysis. Subsequent to the analysis, the instrument location values, modified or unmodified, along with the buffered reference location values may be output to location determination module 136. Since reference location values, instrument location values, and acceleration values may be buffered in order to provide samples for analysis, the mapping of the instrument icon onto the patient image may incur a slight delay relative to interface module 114 of FIG. 8. The buffering and analysis steps may be calibrated so that performance is optimized and the delay is not noticeable by the clinician. In other words, the sampling rate, number of samples buffered, and the complexity of the analysis steps may be selected so that the buffering and analysis steps do not produce a noticeable delay in superimposing the instrument icon onto the patient image.

Filtering module 176 may perform an analysis of the acceleration values in the frequency domain. For example, filtering module 176 may perform an analysis of the frequency content of the acceleration values. In one example, filtering module 176 may implement a Fourier transform (e.g., FFT) on the acceleration values to determine the frequency content of the buffered acceleration values. Filtering module 176 may perform the analysis on the acceleration values in order to detect frequency components present in the acceleration values that may indicate the presence of undesirable acceleration experienced by instrument sensor 110, e.g., acceleration that may result in an incorrect mapping of instrument icon onto the patient image. Undesirable frequency components of acceleration may include components that indicate a rapid change in acceleration, e.g., high frequency components present in the acceleration values. In response to detection of a threshold amount of signal (e.g., a threshold energy) within an undesirable frequency range, filtering module 176 may filter out the undesirable frequency content from the buffered instrument location values.

Frequency components present in the set of acceleration values stored in acceleration buffer module 172 may arise from a variety of different physical effects. For example, frequency components may indicate accelerations due to movement of the heart wall, movements due to breathing, and environmental noise such as a repositioning or bumping of patient 102. Filtering module 176 may detect the presence of any of the above physical effects based on which frequency components are present in the acceleration values. For example, motion of accelerometer 112 due to breathing of the patient may generate a relative lower frequency signal than a heartbeat. In this example, filtering module 176 may detect motion of accelerometer 112 due to the heartbeat, as opposed to breathing, based on detection of a higher frequency component (e.g., a component that includes higher frequency than breathing) in the set of acceleration values.

Filtering module 176 may, after determining the frequency content of the acceleration values, monitor the frequency content of the acceleration values for the presence of a frequency component, or a range of frequencies, that may indicate an undesirable acceleration. For example, a range of frequencies present in the acceleration values due to a heartbeat may be an undesirable range of frequencies since the acceleration imposed on instrument sensor 110 by a heartbeat may cause an incorrect mapping of the instrument icon onto the patient image. If filtering module 176 detects a threshold amount of content (e.g., a threshold energy/power) present at an undesirable frequency, or within an undesirable range of frequencies of the acceleration values, filtering module 176 may filter the buffered instrument location values at the corresponding frequencies to remove the potentially undesirable content and prevent the content from affecting the mapping of the instrument icon. Generally, when such undesirable frequency content is not present in a threshold amount, filtering module 176 may allow the buffered instrument location values to pass through filtering module 176 to location determination module 136 unmodified.

Figure 14:
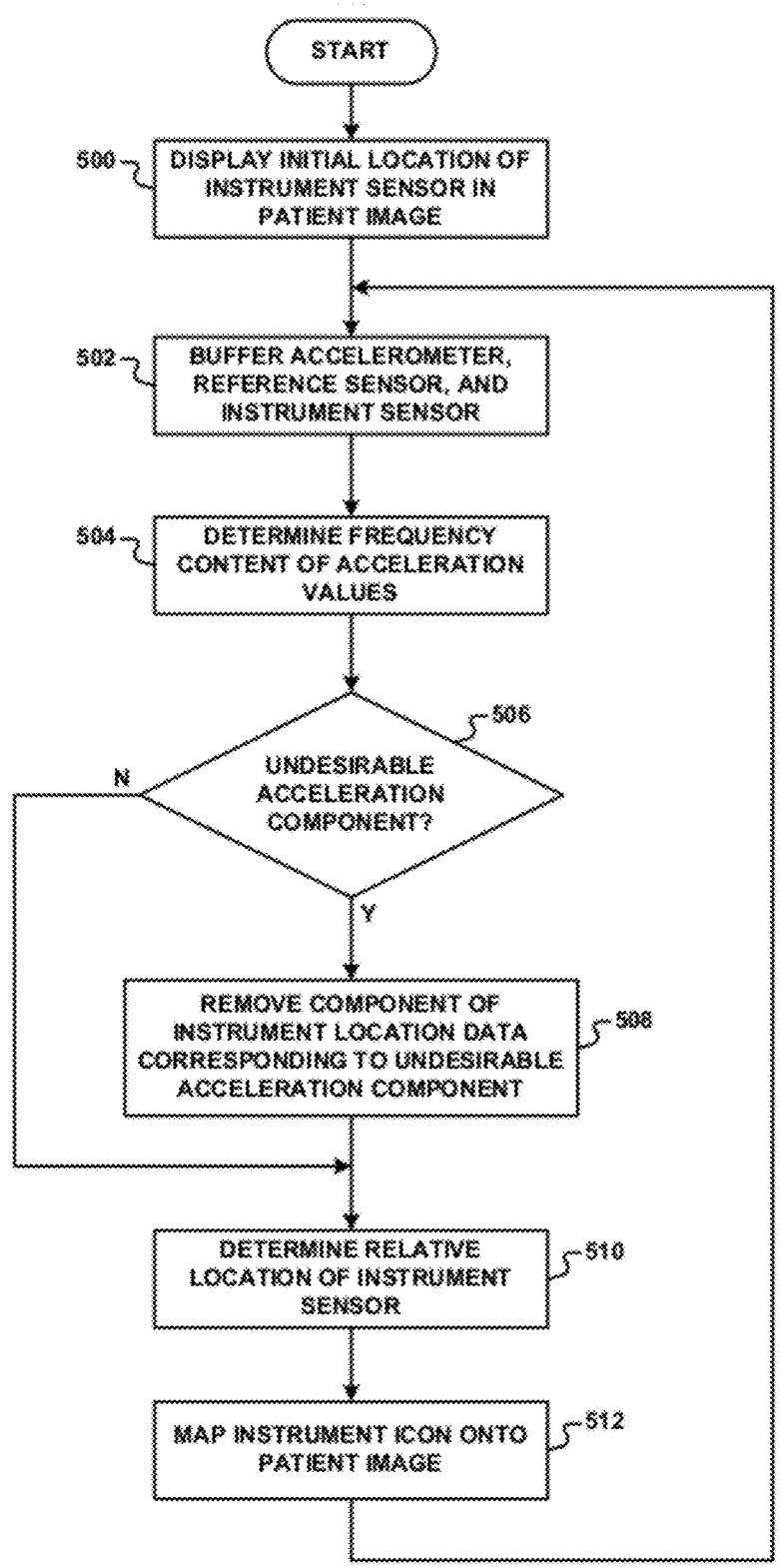
FIG. 14 illustrates an error correction method that includes a filtering operation.

FIG. 14 illustrates an error correction method that includes a filtering operation. Interface module 114 of FIG. 13 may implement the method of FIG. 14. For illustration purposes, it is assumed that the method of FIG. 14 begins during a time when instrument sensor 110 is not experiencing an acceleration that may cause an incorrect mapping of the instrument icon onto the patient image (500).

First, acceleration buffer module 172 buffers acceleration values, instrument buffer module 174 buffers instrument location values, and reference buffer module 178 buffers reference location values (502). Filtering module 176 then determines the frequency content of the acceleration values (504) and determines whether a threshold amount of signal content (e.g., energy/power) is present at undesirable frequencies (506). If the threshold amount of content is present at an undesirable frequency, filtering module 176 filters the buffered instrument location values to remove signal content at the undesirable frequency having the threshold amount of signal content (508). If the threshold amount of content is not present, filtering module 176 allows the buffered instrument location values to pass through to location determination module 136 unmodified. Location determination module 136 determines the relative location of instrument sensor 110 based on either the unfiltered (i.e., unmodified) or filtered (i.e. modified) instrument location values (510). Registration module 138 maps the instrument icon onto the patient image based on the relative location of instrument sensor 110 (512). Display control module 142 then outputs the annotated patient image to display 116.

Figure 15:
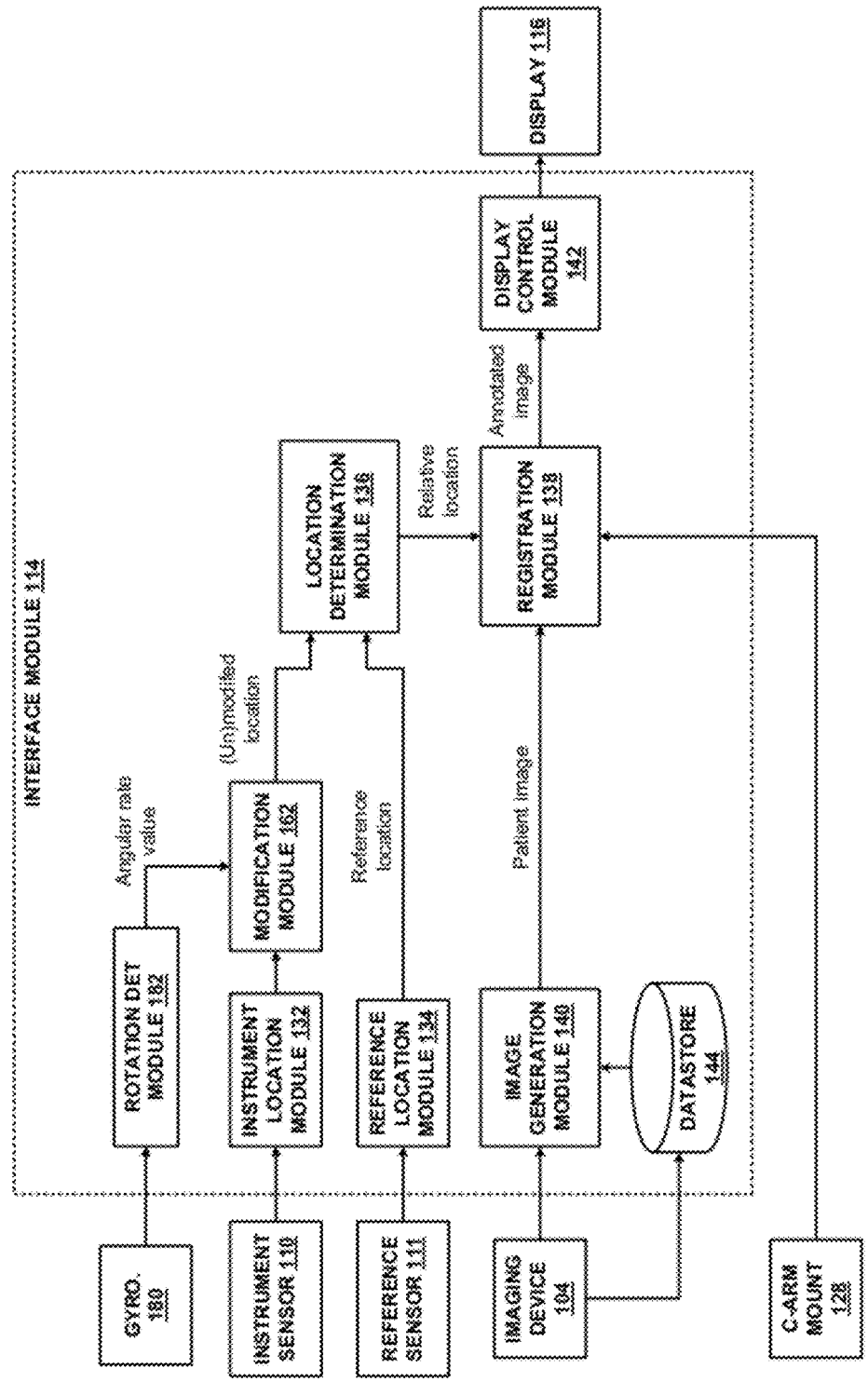
FIG. 15 shows an example interface module that corrects for errors based on a sensed rate of rotation of an instrument.

Referring now to FIG. 15, surgical navigation system 100 may include a gyroscopic sensor 180. Gyroscopic sensor 180 may generate signals indicating an angular orientation and angular rate of rotation (e.g., degrees per second) of gyroscopic sensor 180. Gyroscopic sensor 180 may indicate a rate of angular rotation about one or more axes. Accordingly, when gyroscopic sensor 180 is included on instrument 108, gyroscopic sensor 180 may indicate a rate of angular rotation of instrument 108. In examples where instrument 108 is a catheter, gyroscopic sensor 180 may indicate a rate of angular rotation of the catheter about the long axis of the catheter, or other axes of the catheter, for example. Interface module 114 may receive signals from gyroscopic sensor 180 and determine an angular rate of rotation of gyroscopic sensor 180.

FIG. 15 shows an example interface module 114 that prevents errors due to rotational motion when superimposing an instrument icon on a patient image. Interface module 114 includes a rotation determination module 182 and modification module 162 that prevent image registration errors due to rotational motion of instrument 108. Interface module 114 is connected to gyroscopic sensor 180. Rotation determination module 182 receives signals from gyroscopic sensor 180 and determines a rate of angular rotation of gyroscopic sensor 180. Rotation determination module 182 may determine the rate of angular rotation of gyroscopic sensor 180 around one or more axes, depending on whether gyroscopic sensor 180 generates signals that indicate the rate of rotation of gyroscopic sensor 180 about the one or more axes. Samples taken by rotation determination module 182 of rates of angular rotation may hereinafter be referred to as "angular rate values."

Since instrument sensor 110 may be placed in close proximity with, or mechanically attached to, gyroscopic sensor 180, instrument sensor 110 may move with gyroscopic sensor 180 and experience the same rotation as gyroscopic sensor 180. Therefore, the angular rate values generated by gyroscopic sensor 180 may indicate the rate of rotation experienced by instrument sensor 110, and the angular rate value determined by rotation determination module 182 may indicate the rate of rotation of instrument sensor 110. Thus, rotation determination module 182 may determine a rate of angular rotation experienced by instrument sensor 110 with respect to one or more axes.

Modification module 162 may generate modified or unmodified location values based on the angular rate value determined by rotation determination module 182 and based on one or more locations determined by instrument location module 132. The unmodified location value may be equal to the location of instrument sensor 110 as determined by instrument location module 132. In other words, modification module 162 may generate the unmodified location value by allowing the location of instrument sensor 110, as determined by instrument location module 132, to pass through modification module 162 unchanged.

In general, modification module 162 may generate an unmodified location value when little or no rotation is experienced by instrument sensor 110. In other words, modification module 162 may generate an unmodified location value when instrument sensor 110 is experiencing less than a threshold rate of rotation. However, when a threshold rate of rotation is experienced by instrument sensor 110, modification module 162 may generate a modified location value that is different than the location of instrument sensor 110 as determined by instrument location module 132. For example, the threshold rate of rotation may be based on a rate of rotation that may cause error during the registration process and result in an incorrect mapping of the instrument icon onto the patient image. The threshold rate of rotation may vary depending on the surgical navigation procedure, e.g., the rate at which images are acquired by imaging device 104.

In some examples, the threshold rate of rotation may be based on a rate of rotation that indicates that movement of instrument sensor 110 was not intended by the clinician, but instead caused by a disturbance. For example, in the case where instrument sensor 110 is in a catheter, a rotation imposed on the catheter by a clinician, e.g., when rotating the catheter during the procedure, may be less than the rate of rotation that is imposed on instrument sensor 110 by a heartbeat. Accordingly, in this scenario, the threshold rate of rotation may be selected to be greater than a predicted motion by the clinician, but less than a rate of rotation imposed by a heartbeat, so modification module 162 may generate a modified location value that removes rotation of instrument sensor 110 due to a heartbeat, but not due to rotation by the clinician.

Location determination module 136 determines the relative location of instrument sensor 110 based on the reference location and either the unmodified location value or the modified location value, depending on which is received. Registration module 138 then registers the relative location of instrument sensor 110 on the patient image to generate the annotated image. The annotated image is then output to display 116 by display control module 116.

Figure 16:
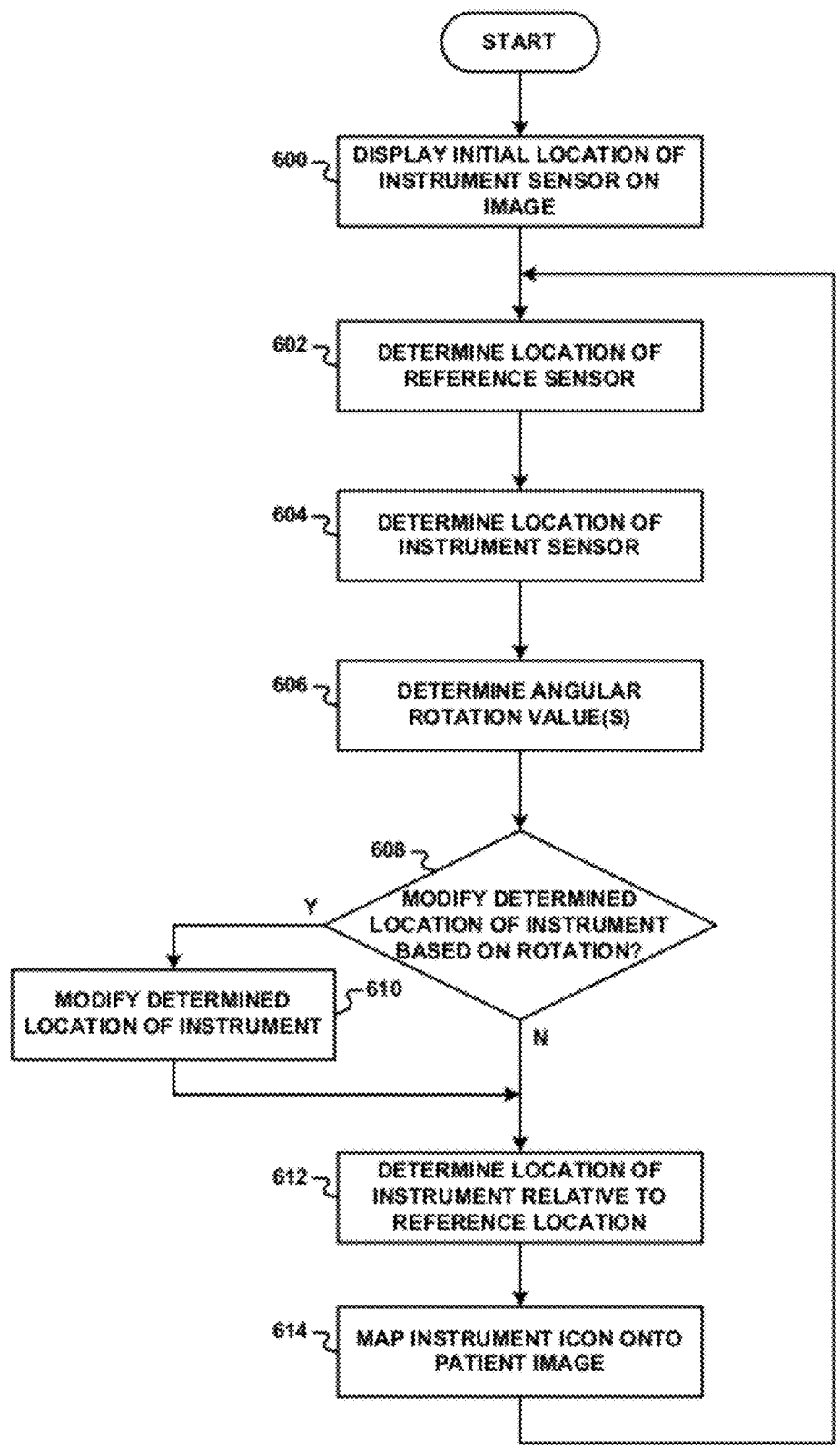
FIG. 16 illustrates an error correction method that corrects for errors due to a rate of rotation of an instrument.

FIG. 16 shows an example error correction method. For illustration purposes, it is assumed that the method begins during a time when instrument sensor 110 is not experiencing a rate of rotation that may cause an error in mapping of the instrument icon onto the patient image. Initially, modification module 162 generates an unmodified location value, and accordingly, the annotated image output by display control module 142 may illustrate the instrument icon in the correct location relative to the patient image (600).

Reference location module 134 determines the location of reference sensor 111 based on reference signals received from reference sensor 111 (602). Instrument location module 132 determines the location of instrument sensor 110 based on instrument location signals received from instrument sensor 110 (604). Rotation determination module 182 determines one or more angular rate values based on gyroscopic signals received from gyroscopic sensor 180 (606).

Modification module 162 then determines whether to generate a modified location value or an unmodified location value based on the one or more angular rate values (608). Modification module 162 may generate the modified location value when the one or more angular rate values indicate that instrument sensor 110 is experiencing a rate of rotation that is greater than the threshold rate of rotation. Modification module 162 may generate an unmodified location value when the angular rate values indicate that instrument sensor 110 is experiencing a rate of rotation that is less than the threshold rate of rotation.

If modification module 162 decides to generate a modified location value, modification module 162 performs one or more modification operations to generate the modified location value (610). Example modifications performed by modification module 162 based on angular rate values may be similar to those performed based on acceleration values as described above.

In some examples, modification module 162 may not modify the instrument location, but instead may allow the instrument location to "pass through" to location determination module 136 as an unmodified location value when the angular rate value is less than the threshold rate of rotation. In these examples, when modification module 162 receives indication that the angular rate value is greater than the threshold rate of rotation, modification module 162 may generate the modified location value. For example, modification module 162 may set the modified location value to a value within a range of previously stored location values that were stored while the angular rate value was less than the threshold rate of rotation. Modification module 162 may output the modified location value for a predetermined period of time or until the rate of rotation experienced by gyroscopic sensor 180 has decreased to a value less than the threshold rate of rotation, for example.

In other examples, modification module 162 may perform an analysis of the angular rate values in the frequency domain. For example, modification module 162 may implement a Fourier transform (e.g., FFT) on the angular rate values to determine the frequency content of buffered angular rate values. Modification module 162 may perform the analysis on the angular rate values in order to detect frequency components present in the angular rate values that may indicate the presence of undesirable rotation experienced by instrument sensor 110, e.g., rotation that may result in an incorrect mapping of instrument icon onto the patient image. In response to detection of a threshold amount of signal (e.g., a threshold energy) within an undesirable frequency range, modification module 162 may filter out the undesirable frequency content from the buffered instrument location values.

Location determination module 136 determines the relative location of instrument sensor 110 based on the reference location and either the modified location value determined in block (610) or the unmodified location value (612). Registration module 138 maps the relative location on the patient image generated by image generation module 140 to generate an annotated image which is output to display 116 via display control module 142 (614).

Although surgical navigation system 100 is illustrated as including accelerometer 112 or gyroscopic sensor 180 separately (e.g., in FIG. 6 and in FIG. 15), in some examples, surgical navigation system 100 may include both accelerometer 112 and gyroscopic sensor 180 along with acceleration determination module 160 and rotation determination module 182.

Various examples have been described. These and other examples are within the scope of the following claims.

The invention claimed is:

1. A medical system comprising:
   a sensor location module configured to determine a location of a magnetic field sensor within a magnetic field;
   a first module configured to detect an acceleration of the magnetic field sensor;
   a modification module configured to:
      compare the detected acceleration of the magnetic field sensor to a threshold acceleration; and
      determine, based on the comparison, whether the detected acceleration of the magnetic field sensor is less than, equal to, or greater than the threshold acceleration; and
   a second module configured to map an icon indicating a modified location of the magnetic field sensor onto an image of a medical patient based on the determination of whether the detected acceleration is less than, equal to, or greater than the threshold acceleration, and one or more previously determined locations, and
   wherein the modification module is configured to:
      store the one or more of the previously determined locations, and
      generate a modified location value based on the detected acceleration of the magnetic field sensor and the one or more of the stored locations,
   wherein the second module is configured to map the icon indicating the location onto the image based on the modified location value, and
   wherein the modification module is configured to, when the detected acceleration of the magnetic field sensor is greater than the threshold acceleration, set the modified location value to a value within a range of the one or more determined locations that were stored when the detected acceleration was less than or equal to the threshold acceleration.

2. The medical system of claim 1, wherein the modification module is further configured to maintain the modified location value at the value within the range for a predetermined period of time after the modification module determines that the detected acceleration of the magnetic field sensor is greater than the threshold acceleration.

3. The medical system of claim 1, wherein the modification module is further configured to maintain the modified location value at the value within the range until the modification module determines that the detected acceleration has decreased to a value less than the threshold acceleration.

4. The medical system of claim 3, wherein the modification module is further configured to set the modified location value to a current location determined by the sensor location module when the detected acceleration of the magnetic field sensor decreases to the value less than the threshold acceleration.

5. The medical system of claim 1, further comprising a display configured to display the icon and the image of the patient.

6. The medical system of claim 5, wherein the icon comprises an instrument icon.

7. The medical system of claim 6, wherein the instrument icon comprises one of a crosshair icon or a graphical representation of an instrument.

8. The medical system of claim 1, wherein the second module is configured to map the icon indicating the modified location of the magnetic field sensor onto the image of the medical patient when it is determined that the detected acceleration is greater than the threshold acceleration, and wherein the second module is configured to map the icon indicating an unmodified location of the magnetic field sensor onto the image of the medical patent when it is determined that the detected acceleration is less than the threshold acceleration.

9. A method comprising:
   determining a location of a magnetic field sensor, in a patient, within a magnetic field;
   detect an acceleration of the magnetic field sensor;
   comparing the detected acceleration of the magnetic field sensor to a threshold acceleration;
   determining, based on the comparison, whether the detected acceleration is less than, equal to, or greater than the threshold acceleration;
   mapping an icon indicating a modified location of the magnetic field sensor onto an image of a medical patient based on the determination of whether the detected acceleration of the magnetic field sensor is less than, equal to, or greater than the threshold acceleration, and one or more previously determined locations;
storing the one or more of the previously determined locations;
generating a modified location value based on the detected acceleration of the magnetic field sensor and the one or more of the stored locations;
mapping the icon indicating the location onto the image based on the modified location value;
determining that the detected acceleration of the magnetic field sensor is greater than the threshold acceleration, and
based on the determination that the detected acceleration of the magnetic field sensor is greater than the threshold acceleration, setting the modified location value to a value within a range of the one or more determined locations that were stored based on the determination that the detected acceleration of the magnetic field sensor was less than or equal to the threshold acceleration.

10. The method of claim 9, further comprising maintaining the modified location value at the value within the range for a predetermined period of time after determining that the detected acceleration of the magnetic field sensor is greater than the threshold acceleration.

11. The method of claim 9, further comprising maintaining the modified location value at the value within the range until determining that the detected acceleration value has decreased to a value less than the threshold acceleration.

12. The method of claim 11, further comprising:
determining that the detected acceleration of the magnetic field sensor decreases to the value less than the threshold acceleration, and
setting the modified location value to a currently determined location based on the determination that the detected acceleration of the magnetic field sensor decreases to the value less than the threshold acceleration.

13. The method of claim 9, further comprising displaying the icon and the image of the patient.

14. The method of claim 13, wherein the icon comprises an instrument icon.

15. The method of claim 14, wherein the instrument icon comprises one of a crosshair icon or a graphical representation of an instrument.

16. The method of claim 9, wherein mapping the icon indicating the modified location of the magnetic field sensor onto the image of the medical patient based on the determination of whether the detected acceleration of the magnetic field sensor is less than, equal to, or greater than the threshold acceleration, and one or more previously determined locations comprises:
determining that the detected acceleration is greater than the threshold acceleration,
mapping the icon indicating the modified location of the magnetic field sensor onto the image of the medical patent based on the determination that the detected acceleration is greater than the threshold acceleration,
determining that the detected acceleration is less than the threshold acceleration; and
mapping the icon indicating an unmodified location of the magnetic field sensor onto the image of the medical patent based on the determination that the detected acceleration is less than the threshold acceleration.

17. A medical system comprising:
a sensor location module configured to determine a location of a magnetic field sensor within a magnetic field;
a first module configured to detect an acceleration of the magnetic field sensor;
a modification module configured to:
compare the detected acceleration of the magnetic field sensor to a threshold acceleration; and
determine, based on the comparison, whether the detected acceleration of the magnetic field sensor is less than, equal to, or greater than the threshold acceleration; and
a second module configured to map an icon indicating a modified location of the magnetic field sensor onto an image of a medical patient based on the determination of whether the detected acceleration is less than, equal to, or greater than the threshold acceleration, and one or more previously determined locations,
wherein the modification module is configured to:
store the one or more of the previously determined locations, and
generate a modified location value based on the detected acceleration of the magnetic field sensor and the one or more of the stored locations,
wherein the second module is configured to map the icon indicating the location onto the image based on the modified location value, and
wherein the modification module is configured to, when the detected acceleration of the magnetic field sensor is greater than the threshold acceleration, set the modified location value equal to one of the one or more determined locations that were stored when the detected acceleration was less than or equal to the threshold acceleration.

18. A medical system comprising:
a sensor location module configured to determine a location of a magnetic field sensor within a magnetic field;
a first module configured to detect an acceleration of the magnetic field sensor;
a modification module configured to:
compare the detected acceleration of the magnetic field sensor to a threshold acceleration; and
determine, based on the comparison, whether the detected acceleration of the magnetic field sensor is less than, equal to, or greater than the threshold acceleration; and
a second module configured to map an icon indicating a modified location of the magnetic field sensor onto an image of a medical patient based on the determination of whether the detected acceleration is less than, equal to, or greater than the threshold acceleration, and one or more previously determined locations, and
wherein the modification module is configured to:
store the one or more of the previously determined locations, and
generate a modified location value based on the detected acceleration of the magnetic field sensor and the one or more of the stored locations,
wherein the second module is configured to map the icon indicating the location onto the image based on the modified location value, and
wherein the modification module is configured to set the modified location value equal to a most recent determined location of the magnetic field sensor in response to the detected acceleration increasing from a value less than the threshold acceleration to a value that is greater than the threshold acceleration.

19. A medical system comprising:
a sensor location module configured to determine a location of a magnetic field sensor within a magnetic field;

a first module configured to detect an acceleration of the magnetic field sensor;
a modification module configured to:
  compare the detected acceleration of the magnetic field sensor to a threshold acceleration; and
  determine, based on the comparison, whether the detected acceleration of the magnetic field sensor is less than, equal to, or greater than the threshold acceleration; and
a second module configured to map an icon indicating a modified location of the magnetic field sensor onto an image of a medical patient based on the determination of whether the detected acceleration is less than, equal to, or greater than the threshold acceleration, and one or more previously determined locations, and
wherein the modification module is configured to:
  store the one or more of the previously determined locations, and
  generate a modified location value based on the detected acceleration of the magnetic field sensor and the one or more of the stored locations,
wherein the second module is configured to map the icon indicating the location onto the image based on the modified location value, and
wherein the modification module is configured to:
  store a plurality of acceleration values representing acceleration detected by the first module;
  store a plurality of location values determined by the sensor location module;
  determine a frequency content of the plurality of acceleration values; and
  generate the modified location value based on analysis of the frequency content.

20. The medical system of claim 19, wherein the modification module is further configured to:
  determine when the acceleration values include greater than a threshold amount of frequency content within a predetermined range of frequencies; and
  filter the plurality of location values to attenuate the predetermined range of frequencies included within the plurality of location values when the acceleration values include greater than the threshold amount of frequency content within the predetermined range of frequencies.

21. A method comprising:
  determining a location of a magnetic field sensor, in a patient, within a magnetic field;
  detecting an acceleration of the magnetic field sensor;
  comparing the detected acceleration of the magnetic field sensor to a threshold acceleration;
  determining, based on the comparison, whether the detected acceleration is less than, equal to, or greater than the threshold acceleration;
  mapping an icon indicating a modified location of the magnetic field sensor onto an image of a medical patient based on the determination of whether the detected acceleration of the magnetic field sensor is less than, equal to, or greater than the threshold acceleration, and one or more previously determined locations;
  storing the one or more of the previously determined locations;
  generating a modified location value based on the detected acceleration of the magnetic field sensor and the one or more of the stored locations;
  mapping the icon indicating the location onto the image based on the modified location value;
  determining that the detected acceleration of the magnetic field sensor is greater than the threshold acceleration; and
  based on the determination that the acceleration of the magnetic field sensor is greater than the threshold acceleration, setting the modified location value equal to one of the one or more determined locations that were stored based on the determination that the detected acceleration of the magnetic field sensor was less than or equal to the threshold acceleration.

22. A method comprising:
  determining a location of a magnetic field sensor, in a patient, within a magnetic field;
  detecting an acceleration of the magnetic field sensor;
  comparing the detected acceleration of the magnetic field sensor to a threshold acceleration;
  determining, based on the comparison, whether the detected acceleration is less than, equal to, or greater than the threshold acceleration;
  mapping an icon indicating a modified location of the magnetic field sensor onto an image of a medical patient based on the determination of whether the detected acceleration of the magnetic field sensor is less than, equal to, or greater than the threshold acceleration, and one or more previously determined locations;
  storing the one or more of the previously determined locations;
  generating a modified location value based on the detected acceleration of the magnetic field sensor and the one or more of the stored locations;
  mapping the icon indicating the location onto the image based on the modified location value;
  determining that the detected acceleration of the magnetic field sensor increases from a value less than the threshold acceleration to a value that is greater than the threshold acceleration, and
  setting the modified location value equal to a most recent determined location of the magnetic field sensor in response to the determination that the detected acceleration of the magnetic field sensor increasing from the value less than the threshold acceleration to the value that is greater than the threshold acceleration.

23. A method comprising:
  determining a location of a magnetic field sensor, in a patient, within a magnetic field;
  detecting an acceleration of the magnetic field sensor;
  comparing the detected acceleration of the magnetic field sensor to a threshold acceleration;
  determining, based on the comparison, whether the detected acceleration is less than, equal to, or greater than the threshold acceleration;
  mapping an icon indicating a modified location of the magnetic field sensor onto an image of a medical patient based on the determination of whether the detected acceleration of the magnetic field sensor is less than, equal to, or greater than the threshold acceleration, and one or more previously determined locations;
  storing the one or more of the previously determined locations;
  generating a modified location value based on the detected acceleration of the magnetic field sensor and the one or more of the stored locations;
  mapping the icon indicating the location onto the image based on the modified location value;
  storing a plurality of acceleration values;
  storing a plurality of location values;

determining a frequency content of the plurality of acceleration values; and generating the modified location value based on analysis of the frequency content.

24. The method of claim 23, further comprising:

determining that the acceleration values include greater than a threshold amount of frequency content within a predetermined range of frequencies; and filtering the plurality of location values to attenuate the predetermined range of frequencies included within the plurality of location values based on the determination that the acceleration values include greater than the threshold amount of frequency content within the predetermined range of frequencies.

* * * * *